United States Patent
Dudee et al.

(10) Patent No.: US 11,705,243 B2
(45) Date of Patent: Jul. 18, 2023

(54) METHOD OF AND SYSTEM FOR DISPLAYING CHANGES IN A MEDICAL STATE OF A PATIENT

(71) Applicants: Jitander Dudee, Lexington, KY (US); Vikram Dudee, Lexington, KY (US)

(72) Inventors: Jitander Dudee, Lexington, KY (US); Vikram Dudee, Lexington, KY (US)

( * ) Notice: Subject to any disclaimer, the term of this patent is extended or adjusted under 35 U.S.C. 154(b) by 20 days.

(21) Appl. No.: 17/391,672

(22) Filed: Aug. 2, 2021

(65) Prior Publication Data

US 2022/0020484 A1 Jan. 20, 2022

Related U.S. Application Data

(63) Continuation of application No. 15/135,835, filed on Apr. 22, 2016, now abandoned.

(60) Provisional application No. 62/150,883, filed on Apr. 22, 2015.

(51) Int. Cl.
*G16H 40/63* (2018.01)
*G16H 10/60* (2018.01)
*G16H 50/30* (2018.01)

(52) U.S. Cl.
CPC ............ *G16H 40/63* (2018.01); *G16H 10/60* (2018.01); *G16H 50/30* (2018.01)

(58) Field of Classification Search
CPC ......... G16H 40/63; G16H 10/60; G16H 50/30
USPC ......................................... 705/2–3
See application file for complete search history.

(56) References Cited

U.S. PATENT DOCUMENTS

| | | | | |
|---|---|---|---|---|
| 6,383,135 B1 * | 5/2002 | Chikovani | ............. | G16H 20/00 |
| | | | | 128/920 |
| 6,438,533 B1 * | 8/2002 | Spackman | ............. | G06Q 10/10 |
| | | | | 706/45 |
| 8,238,999 B2 * | 8/2012 | Haider | .................. | G16H 40/63 |
| | | | | 600/407 |
| 8,792,968 B2 * | 7/2014 | Xiao | ...................... | A61B 5/015 |
| | | | | 382/128 |
| 9,122,776 B2 * | 9/2015 | Dart | .................... | G06F 3/04842 |
| 9,298,182 B2 * | 3/2016 | Joo | ..................... | G05B 23/0272 |
| 2001/0041992 A1 * | 11/2001 | Lewis | ................... | G16H 70/00 |
| | | | | 705/3 |
| 2003/0146942 A1 * | 8/2003 | Helgason | ............... | G16H 10/20 |
| | | | | 705/2 |
| 2004/0230458 A1 * | 11/2004 | Takayama | ............ | G16H 80/00 |
| | | | | 707/999.107 |
| 2011/0077968 A1 * | 3/2011 | Kelly | .................... | G16H 15/00 |
| | | | | 705/2 |

(Continued)

*Primary Examiner* — Michael Tomaszewski
(74) *Attorney, Agent, or Firm* — Black McCuskey

(57) ABSTRACT

A method of managing an electronic health record and displaying a patient's medical state can include receiving a first input corresponding to the medical state, including a first plurality of positives that each correspond to a deviation from a healthy state. The method can also include grouping at least some of the first plurality of positives that collectively correlate to at least one of the medical conditions. The method can also include displaying with a display a statgraph having a plurality of objects including a homunculus plane, nodes projecting away from the plane, axes interconnecting the nodes, and a planar bundling object enveloping at least some of the nodes. The method can also include morphing, on the display controlled by the computing device, a first statgraph into a second statgraph.

20 Claims, 17 Drawing Sheets

(56) References Cited

U.S. PATENT DOCUMENTS

| | | | | |
|---|---|---|---|---|
| 2011/0161854 A1* | 6/2011 | Shukla | ............ | G16H 30/20 |
| | | | | 345/419 |
| 2012/0116804 A1* | 5/2012 | Mesika | ............ | G16H 50/70 |
| | | | | 705/3 |
| 2012/0182291 A1* | 7/2012 | Rawat | ............ | G06T 17/00 |
| | | | | 345/419 |
| 2014/0039925 A1* | 2/2014 | Kelly | ............ | G16H 10/60 |
| | | | | 705/3 |
| 2015/0134361 A1* | 5/2015 | Molenda | ............ | G06Q 10/10 |
| | | | | 705/3 |
| 2015/0278483 A1* | 10/2015 | Pruitt | ............ | G16H 10/60 |
| | | | | 705/3 |

\* cited by examiner

METHOD OF AND SYSTEM FOR DISPLAYING CHANGES IN A MEDICAL STATE OF A PATIENT

CROSS-REFERENCE TO RELATED APPLICATIONS

This application is a continuation application of application Ser. No. 15/135,835 for a METHOD OF AND SYSTEM FOR MANAGING AN ELECTRONIC HEALTH RECORD AND DISPLAYING A MEDICAL STATE OF A PATIENT, filed on Apr. 22, 2016, which is hereby incorporated by reference in its entirety. This application also claims the benefit of U.S. Provisional Patent Application Ser. No. 62/150,883 for a SYSTEM FOR THE GENERATION AND MANAGEMENT OF ELECTRONIC HEALTH RECORDS, filed on 2015 Apr. 22, which is also hereby incorporated by reference in its entirety.

BACKGROUND

1. Field

The present disclosure relates to electronic health record systems, and more particularly relates to graphical displays with which display the physical condition of the patient.

2. Description of Related Prior Art

U.S. Pat. No. 8,792,968 discloses a system and method for health evaluation. The system is an apparatus and a method for human health evaluation utilizing Thermal Micro Texture mapping technology. The method comprises scanning body areas of a patient utilizing an infrared camera, detecting abnormalities in the body of the patient, analyzing abnormalities of the patient against information stored in a database, and reporting results to the patient in a predetermined format. The method provides an earlier discovery of disease by mapping and analyzing abnormal temperatures changes in the body, which can help prevent the disease from progressing at an early stage.

U.S. Pat. No. 9,122,776 discloses an ENHANCED ELECTRONIC HEALTH RECORD GRAPHICAL USER INTERFACE SYSTEM. A user device having a display accesses electronic health records and clinic note templates stored on digital storage segments. A template selection screen is presented on the display of the user device. The template selection screen has at least two view modes. One view mode is a grid view, in which icon representations of various clinic note templates are displayed, each icon representation having a number of secondary icons providing additional functionality and information to the user. Also available is a list view, which also contains a vertical listing of available clinic note templates, each list element also having secondary icons. Upon selection of a template, the user is presented with a formatted clinic note. Additional functionality is available to the user to aid in the efficient capture of information.

U.S. Pat. No. 9,298,182 discloses a METHOD OF DISPLAYING ABNORMAL STATUS IN PLANT OPERATION MONITORING SYSTEM. The disclosure pertains to a method of displaying an abnormal status in a plant operation monitoring system. The method of displaying the abnormal status includes the steps of: receiving information of operational states from a sensor mounted on devices, machines and facilities constituting an industrial plant system; checking any abnormal signal in the operational states, logically grouping parts influencing on operational values when the abnormal signal is generated, and displaying the parts on a piping & instrument drawing (P&ID) on a monitor; and tracing the abnormal signal in a reverse direction of a system flow, searching out the device which causes the abnormal state, and displaying the abnormal device on the piping & instrument drawing.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A method of managing an electronic health record and displaying a patient's medical state to a health care provider can include receiving, at a computing device having one or more processors, a first input corresponding to a first medical state of the patient and including a first plurality of positives. Each of the plurality of positives can correspond to a deviation from a healthy state for a particular anatomical portion of the patient's body and is a numerical value. The method can also include grouping, at the computing device, at least some of the first plurality of positives that collectively correlate to at least one of the plurality of different medical conditions and the respective second plurality of positives. The method can also include displaying, on a display controlled by the computing device, a statgraph having a plurality of objects. The plurality of objects can include a homunculus plane in perspective view. The plane can be divided into a grid of a plurality of cells. At least some of the plurality of cells can correspond to the particular anatomical portions of the patient's body. The plurality of objects can also include a first plurality of nodes each in perspective view. Each node can correspond to one of the first plurality of positives. Each node can project away from the homunculus plane at the cell that corresponds to the respective particular anatomical portion of the patient's body. A height of each of the first plurality of nodes from the homunculus plane can correspond to the respective numerical value. The plurality of objects can also include a first plurality of axes each interconnecting at least two of the first plurality of nodes. The plurality of objects can also include a first planar bundling object in perspective view and enveloping at least some of the first plurality of nodes. The first planar bundling object can be one of transverse and parallel to the homunculus plane and at least partially spaced from the homunculus plane. The method can be executed by a system and can also be embodied in a computer program product comprising program code stored on a non-transitory computer-readable medium. The method can also include morphing, on the display controlled by the computing device, a first statgraph into a second statgraph.

BRIEF DESCRIPTION OF THE DRAWINGS

The detailed description set forth below references the following drawings.

DETAILED DESCRIPTION

Figure 1:
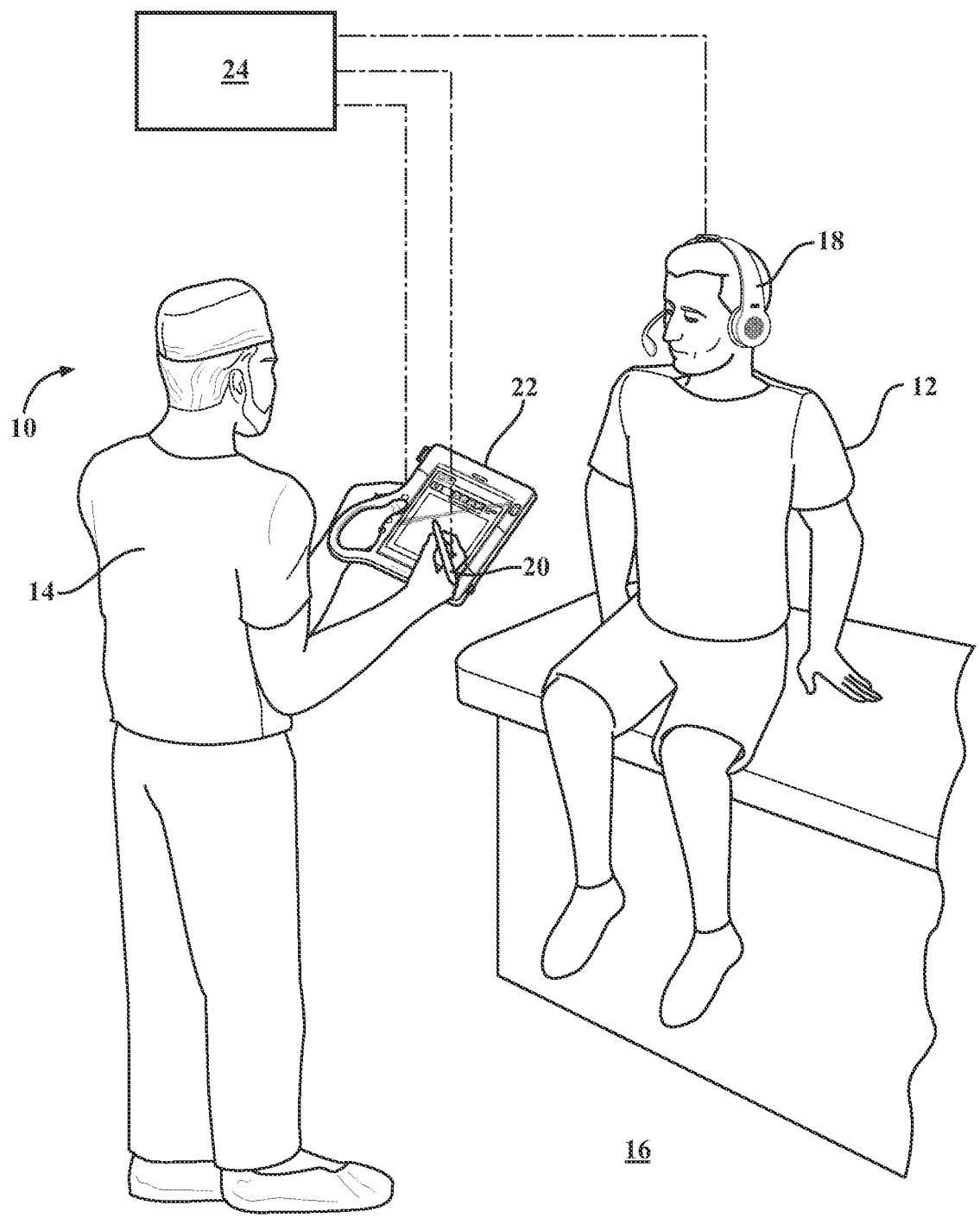
FIG. 1 is a perspective view of a patient interacting with a health care provider according to an exemplary embodiment of the present disclosure.

The inventor has come to appreciate that a major objective in medical record documentation is to demonstrate the level of "work" at each patient visit so that the efficacy of the medical services can be objectively determined. This is not so difficult for discrete activities, such as performance of surgical procedures, but becomes much more difficult when attempting to quantify cognitive effort on the part of the doctor during an office visit. The term "doctor" or "health care provider" is used herein to apply to an individual providing evaluation and management services to a patient, not just actual doctors. By way of example and not limitation, an individual providing evaluation and management services to a patient can be referred to as a provider, a practitioner, or a nurse.

A stereotypical perception exists that doctors have bad handwriting. A major cause of this often justified perception is that doctors have to express detailed assessments of large amounts of information in a written form under pressure of time. Some of this is information is of low value density (when density is expressed as unit of useful information per text character) since it represents essentially a preamble, recap or confirmation of previously obtained information. Interspersed is information of high value density which is unintelligible without the accompanying low value textual information to give it context. Doctors tend to hurry through the formal, verbose sections of their written medical communications sacrificing legibility for speed to focus on what they perceive to be the more important and pertinent expressions. This causes a deterioration in handwriting, initially for the less value dense information but eventually also affecting the sections with higher information value density. Many attempts have been made to reduce this problem by adopting abbreviations and code phrases for common medical concepts, terms, and linkages, but the lack of standardization makes this approach risky and of limited value. More recently, this problem has been tackled by the introduction of electronic health records (hereafter referred to as "EHR" individually) in an attempt to standardize medical notation. Although the problem of illegible handwriting has been largely solved by text entry via keyboard, the current methodology is very burdensome because it increases time and effort required for data entry and makes navigation through a computerized record much more difficult than through a paper chart and causes important information to be diluted and lost within an engulfing sea of text, obscured by ebbing and flowing tides of tabs and windows across the impenetrable computer monitor.

The reality is that most current EHRs generate large volumes of text with very low value density of information when the density of such information is measured across comparable media of visual attention, for example, a paper chart page versus a screenshot of an EHR window open on a monitor or tablet screen. In fact, because doctors have become trained to look for certain penned notations, particularly in relation to their positioning or formatting within a paper chart, the bland presentation of text in an EHR actually hinders communication. The ability to easily manipulate large sections of electronic text, such as by copying and pasting, also creates vulnerabilities to fraud, overutilization of services and repetition of medical errors.

The main purposes of a medical record, traditional or EHR, are to (1) record medical work both cognitive and physical, (2) order, direct and report appropriate therapy at each patient encounter, and (3) communicate the details of the medical assessment of the patient as well as the result of therapy to authorized parties. One or more embodiments of the present disclosure can achieve these three objectives in a consistent and effective manner. Such embodiments can do so by analyzing a change in the medical status of the patient rather than an absolute measure of the patient status to properly calculate the efficiency of medical work. The rate of change of the medical status that is calculated can be applied to measure efficacy of treatment plans.

For such measures of change to be meaningful, the medical status of any individual needs to be described in terms whose magnitude can be quantified to a useful degree and so that the number of constituent elements contributing to these terms is small enough for easy mathematical analysis yet large enough to encompass all the concepts that need to be expressed for practical purposes. Also the depiction of the medical status needs to be in a format so that common patterns of disease complexes are easily recognized by trained staff, and important deviations or anomalies are promptly communicated to the conscious and sub-conscious attention of treating doctors requiring the minimum visual effort.

The constituent elements of the medical status of a patient are based on the following "Descriptive Foundations:"

Subjective backed by objective —medical diagnoses pertaining to self, cohabitants and genetic relatives as well as reported exposure to trauma or disease agents;

Purely Subjective —complaints graded by the nature (location on belts around homunculus) and the degree of suffering;

Objective backed by subjective —measurable elements of biological functional loss; and Purely Objective —doctor identified abnormalities on physical examination listed by pathophysiological observed pathophysiological changes at specific anatomical location.

At each patient visit, the computation of the doctor's work includes recording what tasks and elements of the medical encounter were performed at each visit. The elements are traditionally grouped in to three sections: (1) medical history taking (with various predefined sub-components), (2) physical examination (again with sub-sections related to the specialty), and (3) clinical decision making (also composed of sub-sections such as interpretation of diagnostic tests, ordering of tests, review of other records, communication with other providers and initiation of prescriptions, counseling etc). Existing EHR systems create incentives and disincentives, wherein increasing levels of data input in sections (1) and (2) are only rewarded if the underlying problems addressed in item (3) exceed a certain threshold of risk or complexity. This approach is justified by the rationale that excessive questioning and examination would be wasteful for minor problems. Similarly, existing systems will limit the number of times that conditions only recognized by higher levels (items (1) and (2)) will be reimbursed within a given time period to discourage excess utilization. Such limits may be unfair if a doctor is treating a population with heavy disease burden and will discourage the doctor from attending to such patients. Similarly, sometimes management of complex problems is not reimbursed at a sufficient level simply because a doctor did not document completion of all the elements within the history and the exam because these elements were not considered necessary due to time constraints. One example is a failure to record the social history of a patient who is treated for an urgent injury.

Imperfections of existing systems are only partially recognized. The inventor has also come to appreciate that accommodation or flexibility granted due to the imperfections of existing systems adds to subjective gray areas ripe for abuse. Existing approaches to flexibility rewards those who focus energy on "gaming" the system rather than on patient care.

Most clinical work in the office setting is usually done in elucidating the patient's medical background at the initial visit. Subsequent visits can include elucidating the patient's medical background when the interval over which care is given is relatively long. However, when the patient is seen frequently and in quick succession for a number of overlapping or related problems, it becomes difficult to establish how much new or useful clinical work is done at each visit. Traditionally, a lengthy handwritten note implied that more work had been done. However, a note generated by computer from information entered at an earlier visit, could be copied and pasted into a subsequent encounter by an artful scribe willing to gamble that nothing significant had changed other than the fluid elements of the active problem, and would withstand scrutiny most of the time. Conversely, a skilled clinician can quickly scan several elements of the medical status and hone in on relevant items for deeper inquiry on follow-up visits, and thus perform valuable clinical work with efficiency without necessarily enumerating each item or having their acumen recognized.

The advent of EHRs has thus potentially facilitated overpayment of services for those providers adept at efficiently marking "check boxes" and carrying forward verbose text descriptions rather than those exercising clinical effort accurately. This problem exists because current EHRs are not usually "smart" in that they do not recognize the natural history and chronological evolution of most common medical conditions but instead record a static snapshot, repainted at each visit by rote process.

The present disclosure addresses the multi-layered shortcomings in the art that has been described above. The present disclosure provides a system for the generation and management of electronic health records wherein human disease complexes are described as related groups of positives in the Descriptive Foundations elucidated during the construction of the medical status (creation of the "medical statgraph"). As used herein, a "positive" is an elucidated particular patient reported condition or finding that is a deviation from a baseline healthy condition. The positives in the Descriptive Foundations are graphically depicted as nodes in a grid having a plurality of dimensions and representing medical locations both in the anatomical and abstract (sensory and functional) sense. The grid is composed around a miniature human figure (termed a homunculus) and is infinitely adjustable as three-dimensional structure models are adjustable (zoom, pan, rotate, etc) to any desired level of detail or specificity which will vary from one specialty to another. The homunculus and its satellite regions provide all the location data needed to identify any positives in the Descriptive Foundations. Construction of the statgraph with its attendant positives in the Descriptive Foundations is equivalent to the history and examination portions of the traditional medical consultation (Subjective and Objective parts of a Subjective Objective Assessment Plan or "SOAP note"). The "diagnosis" element of the medical consultation (the Assessment part of the SOAP note) consists of the doctor inferring and declaring etiological associations between the nodes identified as positives on the statgraph to derive "problem bundles." Problem bundles represent the constellation of subjective and objective findings in the proper relative proportion that is typically found in a disease complex of a given severity. A library of standard problem bundles can be formulated from typical disease findings in the general population and can be used to suggest preconfigured problem bundles which may best fit the statgraph under consideration so that the doctor can select these options to remove as many unlinked nodes as possible until those remaining are dismissed as random "noise" or flagged for later investigation until all nodes are reconciled. Each problem bundle of a certain severity or acuity will have a holistic therapy plan associated with it consisting of all necessary elements such as education, medication, medical devices, surgical procedures, additional diagnostic tests, outside consultations and follow up appointments. Each section of such therapy plans will have tiers of treatments intensity guided by current best practices and allowing alternatives in special cases of patient idiosyncrasy without the need to escalate to a whole higher severity level of therapy plan (for example, alternative medications for those who happen to be allergic to the "first line" medication). The activation of the therapy plan and its constituent tasks corresponds to the Plan section of the traditional SOAP note. Computerized order entry is actuated so that the tasks are activated automatically: e.g. printing of instructions, email link to patient portal, e-prescriptions and lab orders generated, fax sent to referring physician, codes and notes sent to insurance carrier, recall reminder sent to calendar etc.

The respective severities of the conditions can be displayed as interconnected bundles. By translating the traditional work steps (history, exam and decision making) into the construction and the monitoring of one or more problem bundles, a more accurate indication of work performed is provided. A problem bundle is a graphical depiction reflecting the patient condition and changes in the display of the problem bundle demonstrate work done to improve the patient's health (rather than game the system). The work done will not be measured by items that can be copied and pasted but by steps which confirm the presence of the problem bundles and describe their dynamic change from the previous assessment. Therefore useful information will be captured and retained at the initial/earlier visit and this work will be recognized, but there will be no reward for copying and pasting this information into subsequent visits because the work to be recognized will be based on and calculated from the severity and number of problem bundles being addressed. The problem bundles once recognized will have to be actively addressed rather than just acknowledged at subsequent visits because they will have an associated therapy plan that has to be modulated. There will be no reward for simply listing a large number of overlapping and potentially duplicative items because the items will have to be assigned to problem bundles if they are to be recognized as part of clinical work. This system rewards coherent analysis and decision making rather than just lengthy descriptions, as has traditionally been the case.

A medical statgraph can be generated by one or more embodiments of the present disclosure. The nature and physical appearance of the medical statgraph will be explained in greater detail below. The medical statgraph can consist of a chronological series of evolving problem bundles juxtaposed over a pictorial representation of the human body and its biological systems with problem bundles representing disease process composed of nodes and interconnected lines. The nodes describe nature and severity of medical findings and the lines represent presumed etiological associations. Problem bundles are fashioned and processed to conform to established constellations of medical symptoms, signs and observations.

A medical statgraph can define a framework for representing the life span of a single patient on which problem bundles are pictorially located. The statgraph is the medical "canvas" of an individual patient taking into account their age and demographics including past diagnoses and treatments. The statgraph can serve as a backdrop to display the chronological evolution of problem bundles under the influence of therapy plans. A new or current statgraph can be generated at the conclusion of each medical encounter by morphing of the statgraph at the last visit. The degree of morphing can be used to calculate the medical work done at that encounter. The nature of the morphing can inform clinical decision making. Projected statgraphs can be generated at the start of a therapeutic plan. The variation from the projected statgraph to an actual statgraph can be used to determine whether therapy plan needs to be altered (escalated, continued, tapered or reconsidered in case of diagnostic confusion).

In an exemplary operating environment for one or more embodiments of the present disclosure, a patient or referring provider can contact a doctor via phone, mail, fax or web to schedule consultation. Contact with the patient can be attempted prior to the patient visit in order to obtain advanced information regarding health issues and other relevant information. A patient record can be created from demographics and/or information can be imported through an electronic practice management system (hereafter "EPM"). The patient's visit can be scheduled in the EPM.

Additional steps can be required for patients with existing paper records who are being seen for the first time after the introduction of electronic medical records. Staff can review, translate and paraphrase past medical history prior to scheduled office visit to create a "current" or "presumed" medical statgraph.

The EHR is modified when a patient visits the doctor's office. After the patient greeted, the patient can be logged in or signed into the EPM and/or EHR. The patient's identity can be verified. The patient can have a unique identifying number and/or photographs can be taken for identification purposes. Other outstanding/additional documentary steps can also be completed, such referrals, preauthorization, past medical records, and previous and current prescriptions. A co-payment can be collected if sum is known in advance.

The patient can be given a welcome package and guided to a reception area. At this point, one or more embodiments of the present disclosure can include requiring the patient to wear an identifying component (also referred to herein as a "first component". The component can be linked to an identifying number associated with the patient as the patient moves from clinical station to station. The component can take the form of a lapel badge; wristband; restaurant type pager; a two-piece, paired headset or earphone/headband; an ear piece; a pair of ear buds extending from a tag; or smart glasses. The patient can be given the first component and placed in a row or file along with other patients according to their turn.

FIG. 1 is a perspective view of an operating embodiment for a computing device 10 according to an exemplary embodiment of the present disclosure. It should be appreciated that a computing device 10 according to one or more implementations of the present disclosure can be cooperatively defined by structures that are physically remote from one another, such, for example, a server and a tablet, or a tablet and a stylus, or a patient wearable device and a server. Examples of computing devices or portions of computing devices can include desktop computers, laptop computers, tablet computers, mobile phones, and smart televisions.

In FIG. 1, a patient 12 is interacting with a healthcare provider 14 according to an exemplary embodiment of the present disclosure in an examination room 16. The patient 12 is wearing a first component 18 of the computing device 10. The first component 18 can be a device wearable by the patient 12. The healthcare provider 14 can be using a second component 20 and a third component 22 of the computing device 10. The exemplary second component 20 can be shaped as a stylus. The third component 22 can be defined by a tablet computer. A fourth component 24 of the computing device 10 can be a server. The fourth component 24 can be positioned in the same building as the examination room 16 or remote from the building containing the examination room 16. All of the components 18, 20, 22 can be communicating data about the patient's medical state to the component 24 for storage and processing.

Figure 1A:
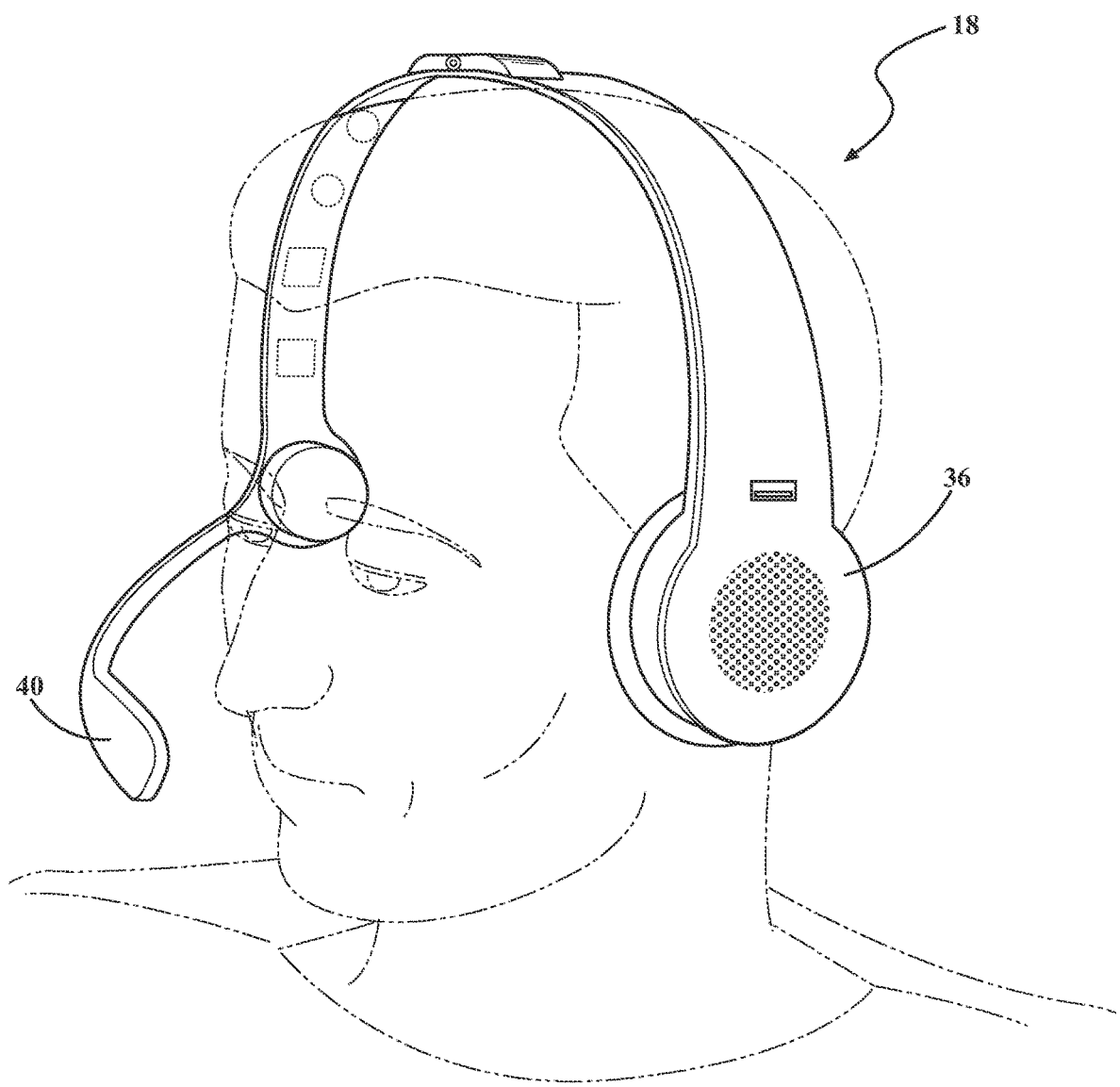
FIG. 1A is a perspective view of a first component of an exemplary computing device according to some implementations of the present disclosure.
Figure 2:
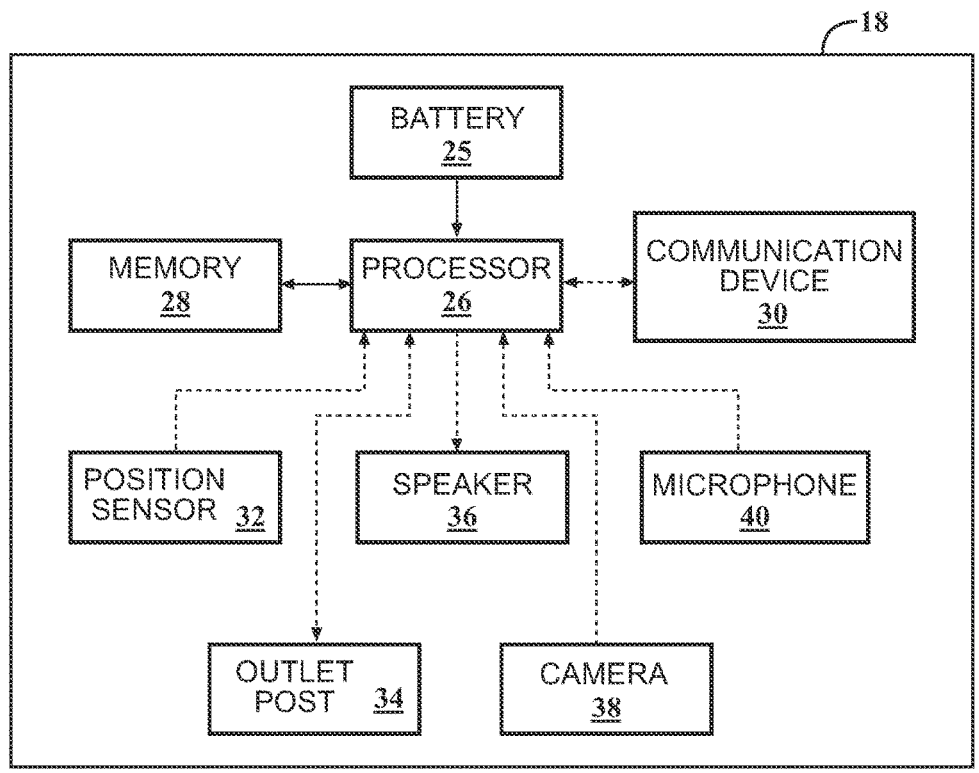
FIG. 2 is a functional block diagram of the first component of an exemplary computing device according to some implementations of the present disclosure.

FIG. 2 is a functional block diagram of the first component 18 of an exemplary computing device 10 according to some implementations of the present disclosure. The first component 18 can take the form of a headset as shown in FIG. 1A. The first component 18 can be used to summon the patient, confidentially communicate information, and to broadcast audio recordings tailored for the patient. The first component 18 can include a processor 26, memory 28, transceiver or communication device 30, a position sensor 32, an outlet port 34, speaker 36, camera 38, and a microphone 40. The first component 18 can also include a battery 25 providing power to the other modules of the first component 18.

The processor 26 can be configured to control operation of the first component 18 of the computing device 10. It should be appreciated that the term "processor" as used herein can refer to both a single processor and two or more processors operating in a parallel or distributed architecture. The processor 26 can operate under the control of an operating system, kernel and/or firmware and can execute or otherwise rely upon various computer software applications, components, programs, objects, modules, data structures, etc. Moreover, various applications, components, programs, objects, modules, etc. may also execute on one or more processors in another computing device coupled to processor 26, e.g., in a distributed or client-server computing environment, whereby the processing required to implement the functions of embodiments of the present disclosure may be allocated to multiple computers over a network. The processor 26 can be configured to perform general functions including, but not limited to, loading/executing an operating system of the computing device 10, controlling communication via the communication device 30, and controlling read/write operations at the memory 28. The processor 26 can also be configured to perform specific functions relating to at least a portion of the present disclosure including, but not limited to, collecting and reporting patient-related health data, facilitating communication between the patient 12 and the healthcare provider 14, reporting the position of the patient 12 in the healthcare facility.

Memory 28 can be defined in various ways in implementations of the present disclosure. Memory 28 can include computer readable storage media and communication media. Memory 28 can be non-transitory in nature, and may include volatile and non-volatile, and removable and non-removable media implemented in any method or technology for storage of information, such as computer-readable instructions, data structures, program modules or other data. Memory 28 can further include RAM, ROM, erasable programmable read-only memory (EPROM), electrically erasable programmable read-only memory (EEPROM), flash memory or other solid state memory technology, CD-ROM, digital versatile disks (DVD), or other optical storage, magnetic cassettes, magnetic tape, magnetic disk storage or other magnetic storage devices, or any other medium that can be used to store the desired information and which can be accessed by the processor 26. Memory 28 can store computer readable instructions, data structures or other program modules. By way of example, and not limitation, communication media may include wired media such as a wired network or direct-wired connection, and wireless media such as acoustic, RF, infrared and other wireless media. Combinations of any of the above may also be included within the scope of computer readable media.

The transceiver or communication device 30 is configured for communication between the processor 26 and other devices, e.g., the component 24, via a network. The network can include a local area network (LAN), a wide area network (WAN), e.g., the Internet, or a combination thereof. Specifically, the communication device 30 can transmit and receive communications between the patient 12 and the healthcare provider 14, video generated by the camera 38, and the position of the patient 12 sensed by the position sensor 32.

The position sensor 32 can be configured to generate a position signal indicative of the position of the patient 12 within the healthcare facility. The position sensor 32 can be configured to detect an absolute or relative position of the patient 12 wearing the first component 18. The position sensor can transmit information regarding lateral juxtaposition of anatomical sites in relation to diagnostic or therapeutic instruments to reduce the risk of site errors, For example, to differentiate the left eye or ear from the right eye or ear. The position sensor 32 can electrically communicate a position signal containing position data to the processor 26 and the processor 26 can control the communication device 30 to transmit the position signal to the fourth component 24 through a network. Identifying the position of the patient 12 can be accomplished by radio, ultrasound or ultrasonic, infrared, or any combination thereof. The position sensor 32 can be a component of a real-time locating system (RTLS), which is used to identify the location of objects and people in real time within a building such as a healthcare facility. The position sensor 32 can include a tag that communicates with fixed reference points in the healthcare facility. The fixed reference points can receive wireless signals from the position sensor 32. The position signal can be processed to assist in determining one or more items that are proximate to the patient 12 and are visible in the video signal. The fourth component 24 can receive position data, identify the location of the patient 12, and communicate the position date the third component 22 in some embodiments of the present disclosure.

The outlet port 34 can allow the extraction of data stored in memory 28. The configuration of the outlet port 34 can be selected as desired. By way of example and not limitation, the outlet port 34 can be a USB-A, USB-B, Mini-A & Mini-B, Micro-B, or Micro-AB.

The speaker 36 can be configured to emit sounds, messages, information, and any other audio signal to the patient 12. The speaker 36 can be positioned within the range of hearing of the patient 12. Audio content transmitted by the fourth component 24 can be played for the patient 12 through the speaker 36. The communication device 30 can receive the audio signal from the fourth component 24 and direct the audio signal to the processor 26. The processor 26 can then control the speaker 36 to emit the audio content.

The camera 38 can be configured to generate a video signal. The camera 38 can be oriented to generate a video signal that approximates the field of view of the patient 12 wearing the first component 18. The camera 38 can be operable to capture single images and/or video and to generate a video signal based thereon.

The microphone 40 can be configured to generate an audio signal that corresponds to sound generated by and/or proximate to the patient 12. The audio signal can be processed by the processor 26 or by the fourth component 24. Such audio signals can be correlated to the video recording.

Figure 3:
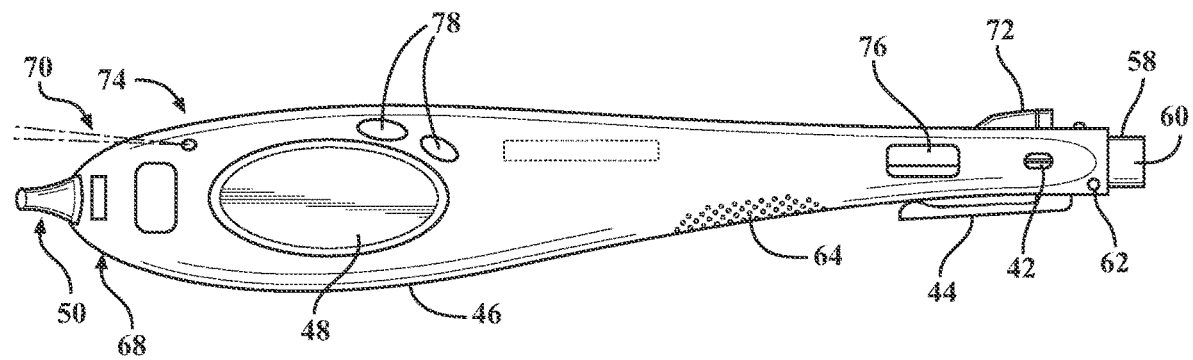
FIG. 3 is a perspective view of a second component of an exemplary computing device according to some implementations of the present disclosure.
Figure 4:
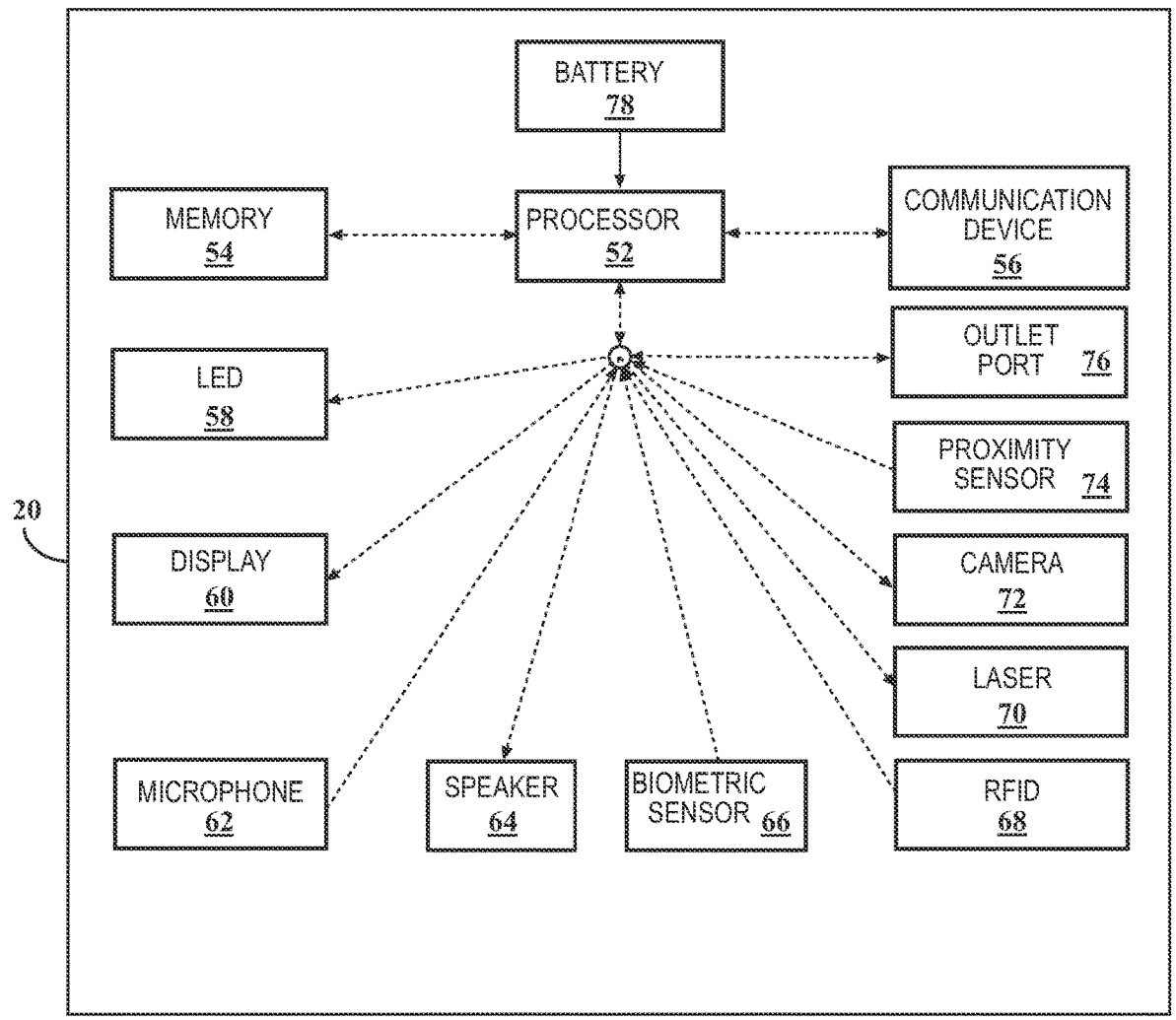
FIG. 4 is a functional block diagram of the second component of an exemplary computing device according to some implementations of the present disclosure.

FIG. 3 is a perspective view of the second component 20 and FIG. 4 is a functional block diagram of the second component 20. As shown in FIG. 3, the second component 20 can include a plurality of mechanical features including a lanyard aperture 42, a clip 44 for holding the second component 20 in a pocket, a rubber or elastomeric gripping surface 46, a receptacle 48 for receiving a finger, a tip 50 for supporting a writing instrument or a rubber tip for engaging a touch screen, and one or more buttons 78 engageable with a thumb or fingers. As shown in FIG. 3, the second component 20 can include a plurality of electrical features including a processor 52, memory 54, a communication device 56, a light emitting diode (LED) 58, a display 60, a microphone 62, a speaker 64, a biometric sensor 66, a radio frequency identification (RFID) chip 68, a laser 70, a camera 72, a proximity sensor 74, and an outlet port 76. The second component 20 can also include a battery 78 providing power to the other modules of the second component 20.

The processor 52 can be configured to control operation of the second component 20 of the computing device 10. It should be appreciated that the term "processor" as used herein can refer to both a single processor and two or more processors operating in a parallel or distributed architecture. The processor 52 can operate under the control of an operating system, kernel and/or firmware and can execute or otherwise rely upon various computer software applications, components, programs, objects, modules, data structures, etc. Moreover, various applications, components, programs, objects, modules, etc. may also execute on one or more processors in another computing device coupled to processor 52, e.g., in a distributed or client-server computing environment, whereby the processing required to implement the functions of embodiments of the present disclosure may be allocated to multiple computers over a network. The processor 52 can be configured to perform general functions including, but not limited to, loading/executing an operating system of the computing device 10, controlling communication via the communication device 56, and controlling read/write operations at the memory 54. The processor 52 can also be configured to perform specific functions relating to at least a portion of the present disclosure including, but not limited to, collecting and reporting patient-related health data.

Memory 54 can be defined in various ways in implementations of the present disclosure. Memory 54 can include computer readable storage media and communication media. Memory 54 can be non-transitory in nature, and may include volatile and non-volatile, and removable and non-removable media implemented in any method or technology for storage of information, such as computer-readable instructions, data structures, program modules or other data. Memory 54 can further include RAM, ROM, erasable programmable read-only memory (EPROM), electrically erasable programmable read-only memory (EEPROM), flash memory or other solid state memory technology, CD-ROM, digital versatile disks (DVD), or other optical storage, magnetic cassettes, magnetic tape, magnetic disk storage or other magnetic storage devices, or any other medium that can be used to store the desired information and which can be accessed by the processor 52. Memory 54 can store computer readable instructions, data structures or other program modules. By way of example, and not limitation, communication media may include wired media such as a wired network or direct-wired connection, and wireless media such as acoustic, RF, infrared and other wireless media. Combinations of any of the above may also be included within the scope of computer readable media.

The transceiver or communication device 56 is configured for communication between the processor 52 and other devices, e.g., the component 24, via a network. The network can include a local area network (LAN), a wide area network (WAN), e.g., the Internet, or a combination thereof. Specifically, the communication device 56 can transmit and receive patient-related data associated with the medical state of the patient 12, from the second component 20 to the fourth component 24 or the third component 22.

The LED 58 can be controlled by the processor 52 to emit light as desired. Light can be desirable to illuminate a portion of the body of the patient 12. The display 60 can be configured to display video content. The display 60 can be configured to display text, graphics, images, illustrations and any other video signals to the patient 12 or the healthcare provider 14. The microphone 62 can be configured to generate an audio signal that corresponds to sound generated by and/or proximate to the patient 12, such as the voice of the patient 12 or the voice of the healthcare provider 14. The audio signal can be processed by the processor 52 or by the fourth component 24. Such audio signals can be correlated to any video recording. The speaker 64 can be configured to emit sounds, messages, information, and any other audio signal to the patient 12 or the healthcare provider 14.

The biometric sensor 66 can be positioned at the bottom or innermost portion of the receptacle 48. The biometric sensor 66 can be utilized to verify the identity of the healthcare provider 14 or the patient 12. The RFID chip 68 can be utilized to identify a particular second component 20 from a plurality of similar second components. The laser 70 can be operable to generate a laser beam that can be utilized during the examination of the patient 12. The camera 72 can be configured to generate a video signal. The camera 72 can be operable to capture single images and/or video and to generate a video signal based thereon. The video signal can include images associated with the patient 12. The outlet port 76 can allow the extraction of data stored in memory 54. The configuration of the outlet port 76 can be selected as desired. By way of example and not limitation, the outlet port 76 can be a USB-A, USB-B, Mini-A & Mini-B, Micro-B, or Micro-AB.

Figure 5:
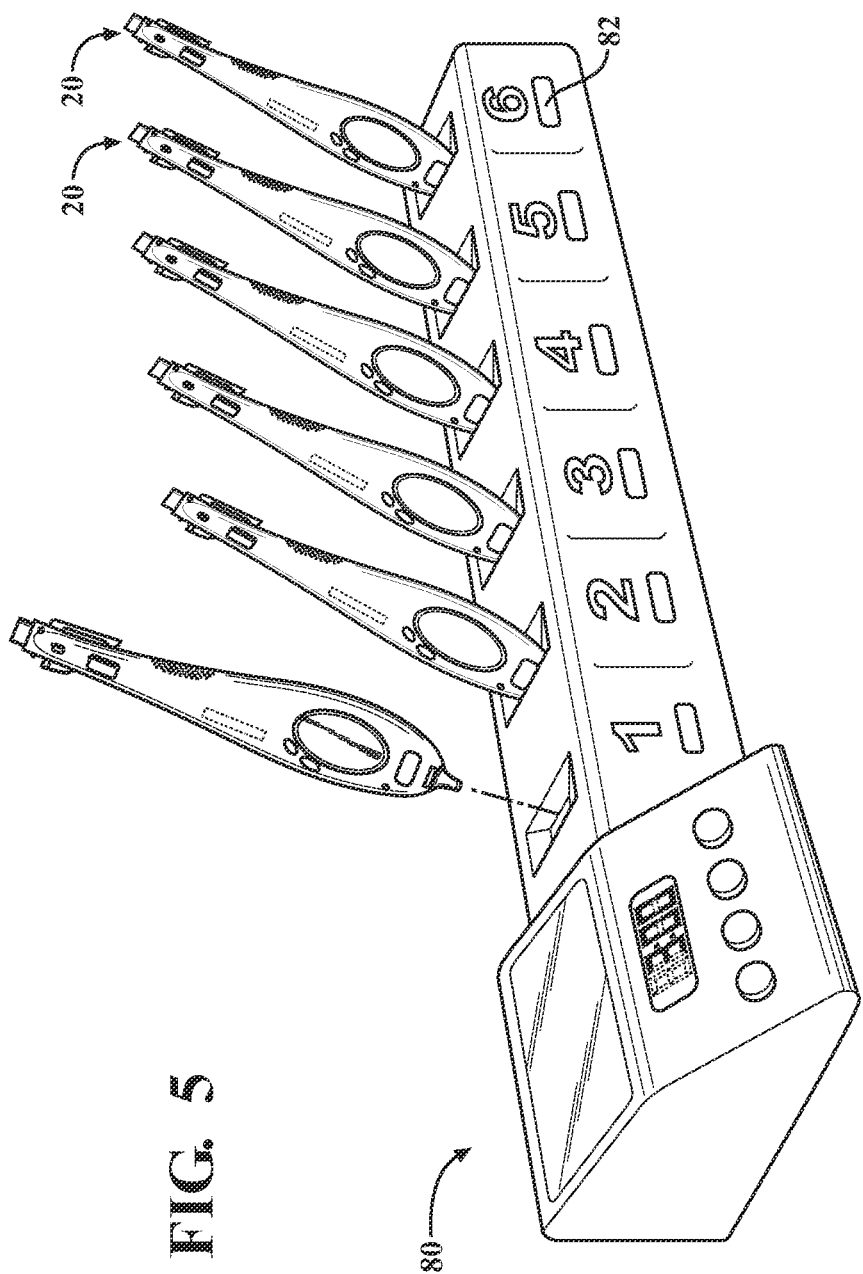
FIG. 5 is a perspective view of a retaining station for a plurality of second components.

FIG. 5 is a perspective view of a retaining station 80 for a plurality of second components 20. Each of the second components 20 can be stored in a slot or holding pen of the retaining station 80. The retaining station 80 can include one or more locking mechanisms to retain the second components 20. Each lock can be selectively unlocked through the use of a biometric sensor, such as referenced at 82. Each healthcare provider 14 can engage the particular biometric sensor to release his/her second component 20. The unlocking of the second component 20 can also trigger the start of the work shift of the healthcare provider 14, or the "clocking in" of the healthcare provider 14.

Figure 6:
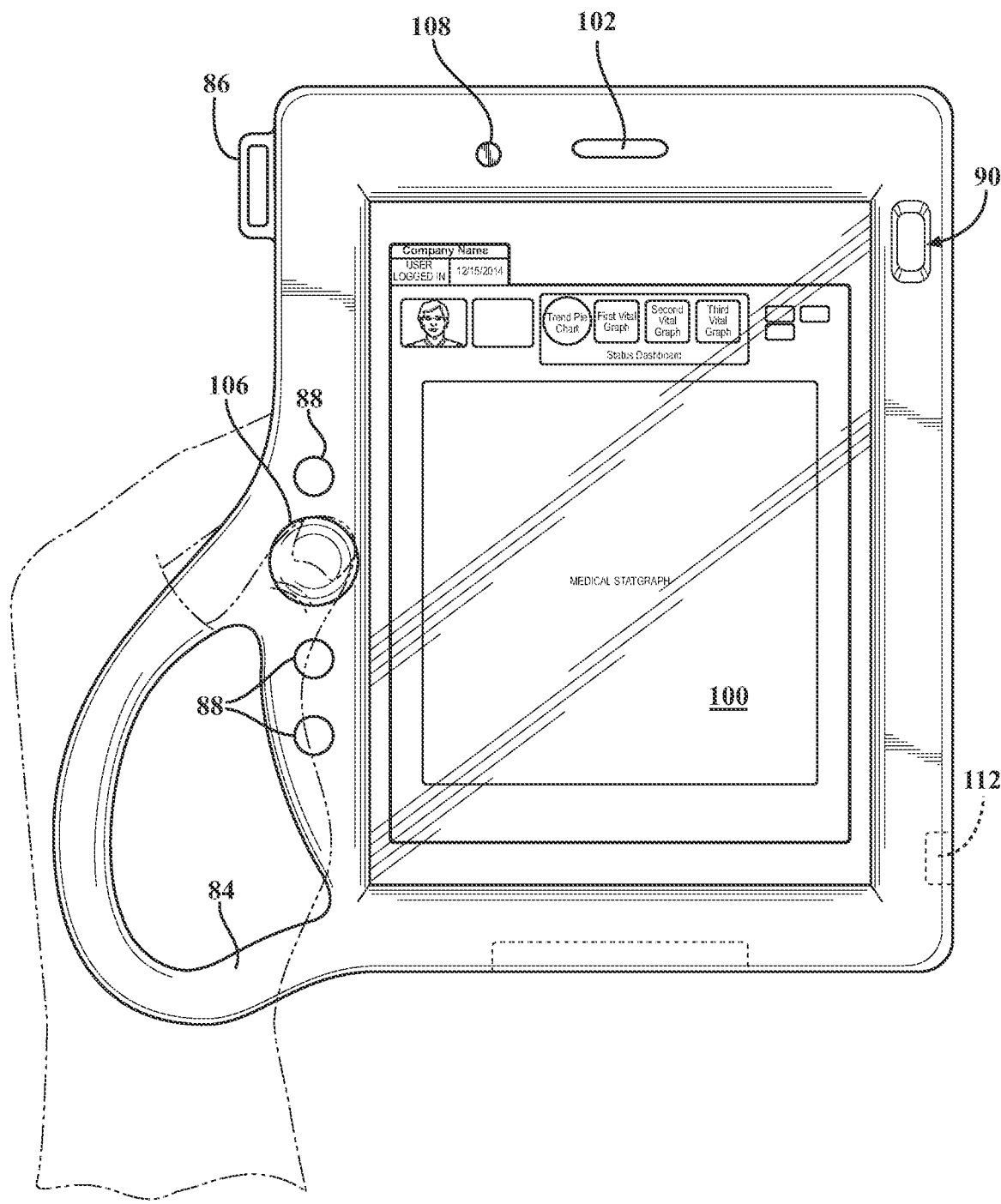
FIG. 6 is a front view of a third component of an exemplary computing device according to some implementations of the present disclosure.
Figure 7:
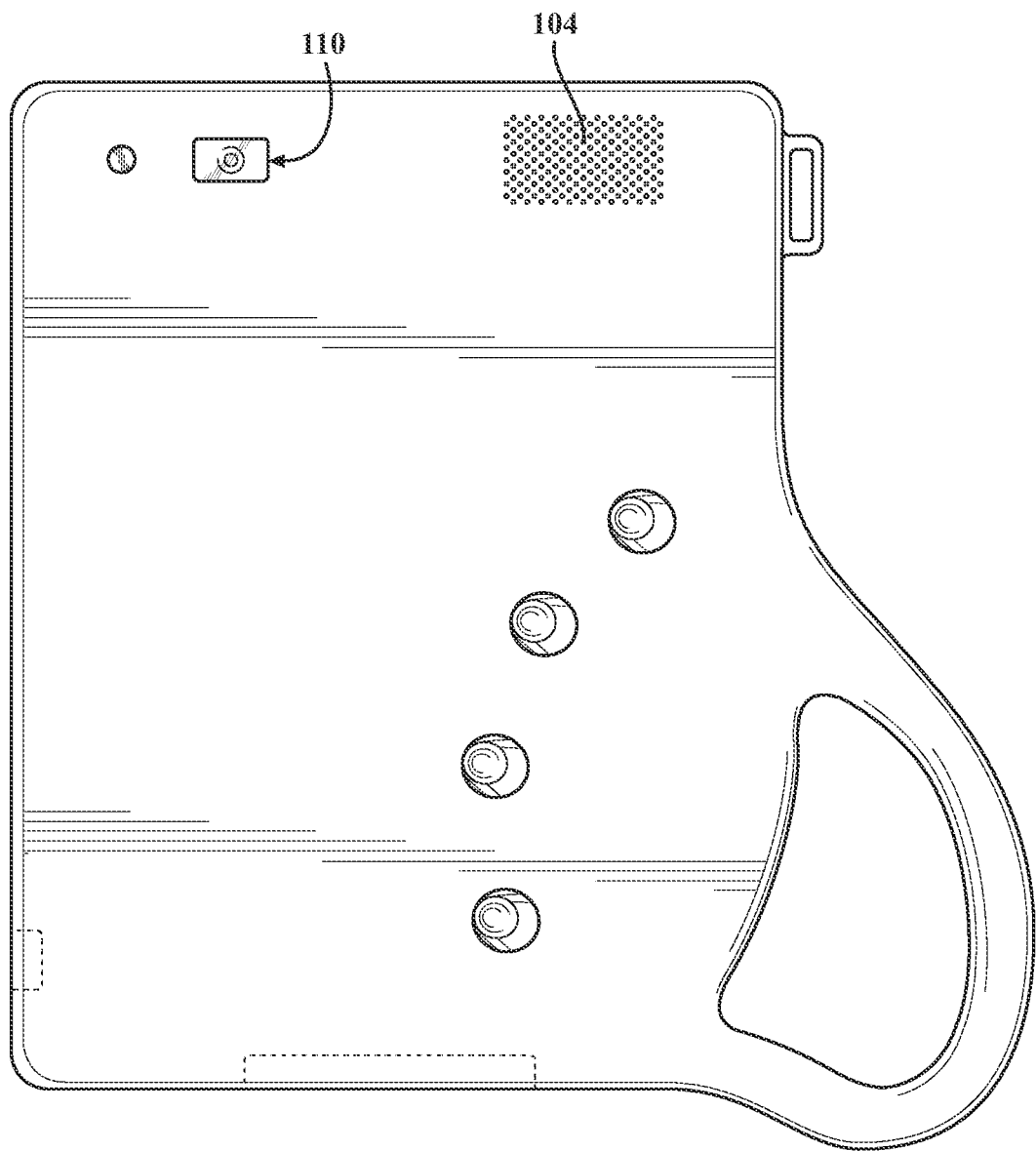
FIG. 7 is a back view of the third component of an exemplary computing device according to some implementations of the present disclosure.
Figure 8:
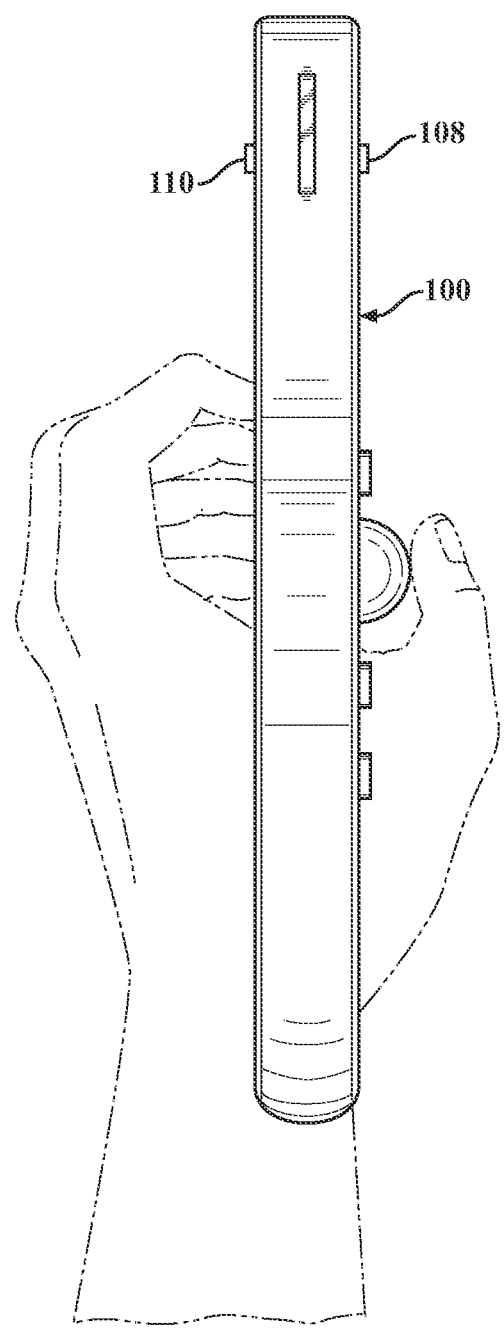
FIG. 8 is a side view of the third component of an exemplary computing device according to some implementations of the present disclosure.
Figure 9:
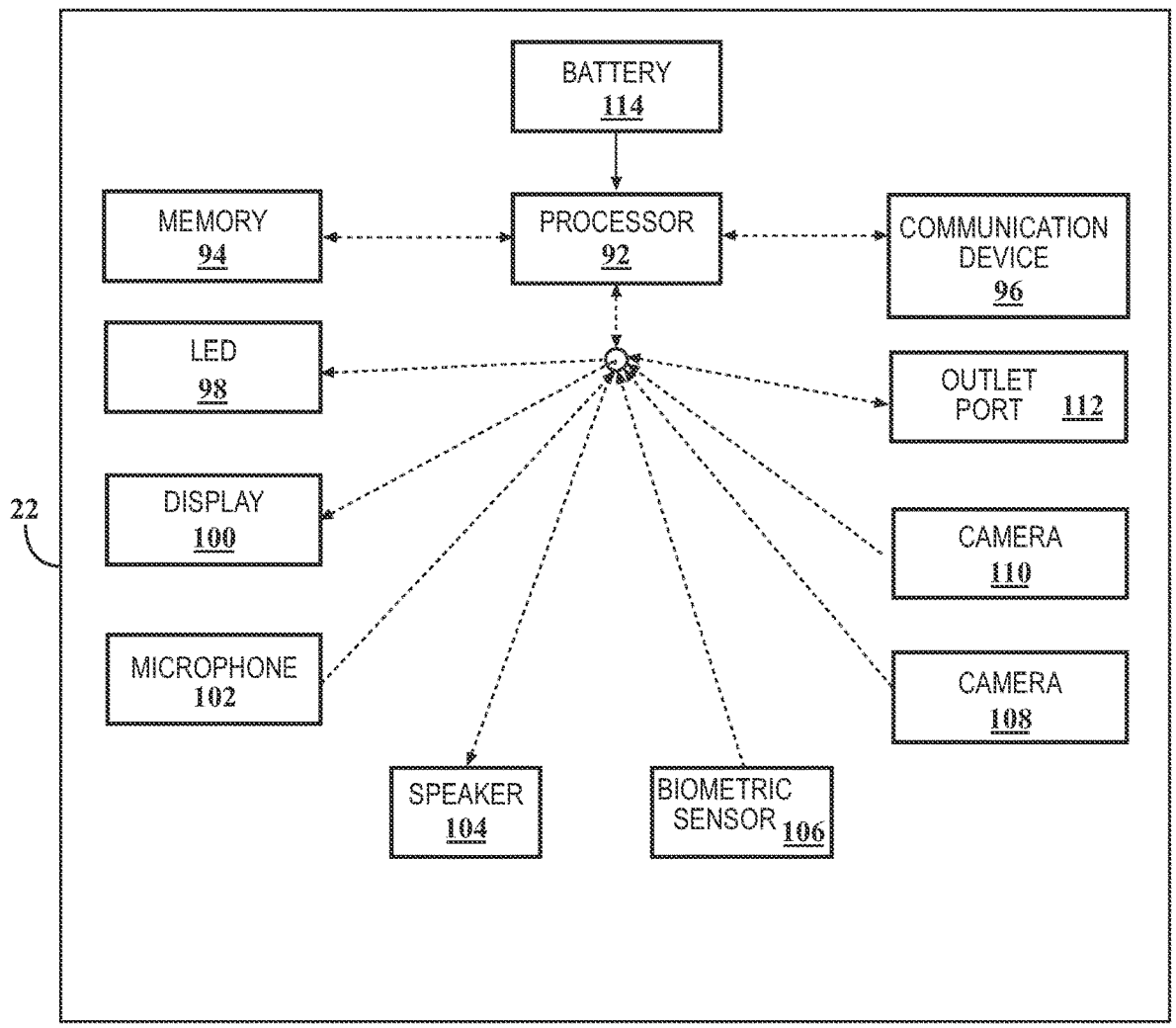
FIG. 9 is a functional block diagram of the third component of an exemplary computing device according to some implementations of the present disclosure.

FIG. 6 is a front view of the third component 22, FIG. 7 is a back view, and FIG. 8 is a side view. FIG. 9 is a functional block diagram of the third component 22. As shown in FIGS. 6-8, the third component 22 can include a plurality of mechanical features including a handle 84, a clip 86 for receiving a strap, one or more buttons 88 engageable with a thumb or fingers, and a receptacle 90 for receiving the second component 20. As shown in FIG. 9, the third component 22 can include a plurality of electrical features including a processor 92, memory 94, a communication device 96, a light emitting diode (LED) 98, a display 100, a microphone 102, a speaker 104, a biometric sensor 106, cameras 108 and 110, and an outlet port 112. The third component 22 can also include a battery 114 providing power to the other modules of the third component 22.

The processor 92 can be configured to control operation of the third component 22 of the computing device 10. It should be appreciated that the term "processor" as used herein can refer to both a single processor and two or more processors operating in a parallel or distributed architecture. The processor 92 can operate under the control of an operating system, kernel and/or firmware and can execute or otherwise rely upon various computer software applications, components, programs, objects, modules, data structures, etc. Moreover, various applications, components, programs, objects, modules, etc. may also execute on one or more processors in another computing device coupled to processor 92, e.g., in a distributed or client-server computing environment, whereby the processing required to implement the functions of embodiments of the present disclosure may be allocated to multiple computers over a network. The processor 92 can be configured to perform general functions including, but not limited to, loading/executing an operating system of the computing device 10, controlling communication via the communication device 96, and controlling read/write operations at the memory 94. The processor 92 can also be configured to perform specific functions relating to at least a portion of the present disclosure including, but not limited to, collecting and reporting patient-related health data.

Memory 94 can be defined in various ways in implementations of the present disclosure. Memory 94 can include computer readable storage media and communication media. Memory 94 can be non-transitory in nature, and may include volatile and non-volatile, and removable and non-removable media implemented in any method or technology for storage of information, such as computer-readable instructions, data structures, program modules or other data. Memory 94 can further include RAM, ROM, erasable programmable read-only memory (EPROM), electrically erasable programmable read-only memory (EEPROM), flash memory or other solid state memory technology, CD-ROM, digital versatile disks (DVD), or other optical storage, magnetic cassettes, magnetic tape, magnetic disk storage or other magnetic storage devices, or any other medium that can be used to store the desired information and which can be accessed by the processor 92. Memory 94 can store computer readable instructions, data structures or other program modules. By way of example, and not limitation, communication media may include wired media such as a wired network or direct-wired connection, and wireless media such as acoustic, RF, infrared and other wireless media. Combinations of any of the above may also be included within the scope of computer readable media.

The transceiver or communication device 96 is configured for communication between the processor 92 and other devices, e.g., the component 24, via a network. The network can include a local area network (LAN), a wide area network (WAN), e.g., the Internet, or a combination thereof. Specifically, the communication device 96 can transmit and receive patient-related data associated with the medical state of the patient 12, from the third component 22 to the fourth component 24 or the second component 20.

The LED 98 can be controlled by the processor 92 to emit light as desired. Light can be desirable to illuminate a portion of the body of the patient 12 or, as set forth below, to render the third component 22 more easily visible. The display 100 can be configured to display video content. The display 100 can be configured to display text, graphics, images, illustrations and any other video signals to the patient 12 or the healthcare provider 14. Data from the EHR of the patient 12 can be displayed on the display 100. A graphic user interface for entering input to the EHR of the patient 12 can be displayed on the display 100. The microphone 102 can be configured to generate an audio signal that corresponds to sound generated by and/or proximate to the patient 12, such as the voice of the patient 12 or the voice of the healthcare provider 14. The audio signal can be processed by the processor 92 or by the fourth component 24. Such audio signals can be correlated to any video recording. The speaker 104 can be configured to emit sounds, messages, information, and any other audio signal to the patient 12 or the healthcare provider 14.

The biometric sensor 106 can be utilized to verify the identity of the healthcare provider 14 or the patient 12. The cameras 108, 110 can be configured to generate a video signal. The cameras 108, 110 can be operable to capture single images and/or video and to generate a video signal based thereon. The video signal can include images associated with the patient 12 or the healthcare provider 14. The outlet port 112 can allow the extraction of data stored in memory 94. The configuration of the outlet port 112 can be selected as desired. By way of example and not limitation, the outlet port 112 can be a USB-A, USB-B, Mini-A & Mini-B, Micro-B, or Micro-AB.

Figure 10:
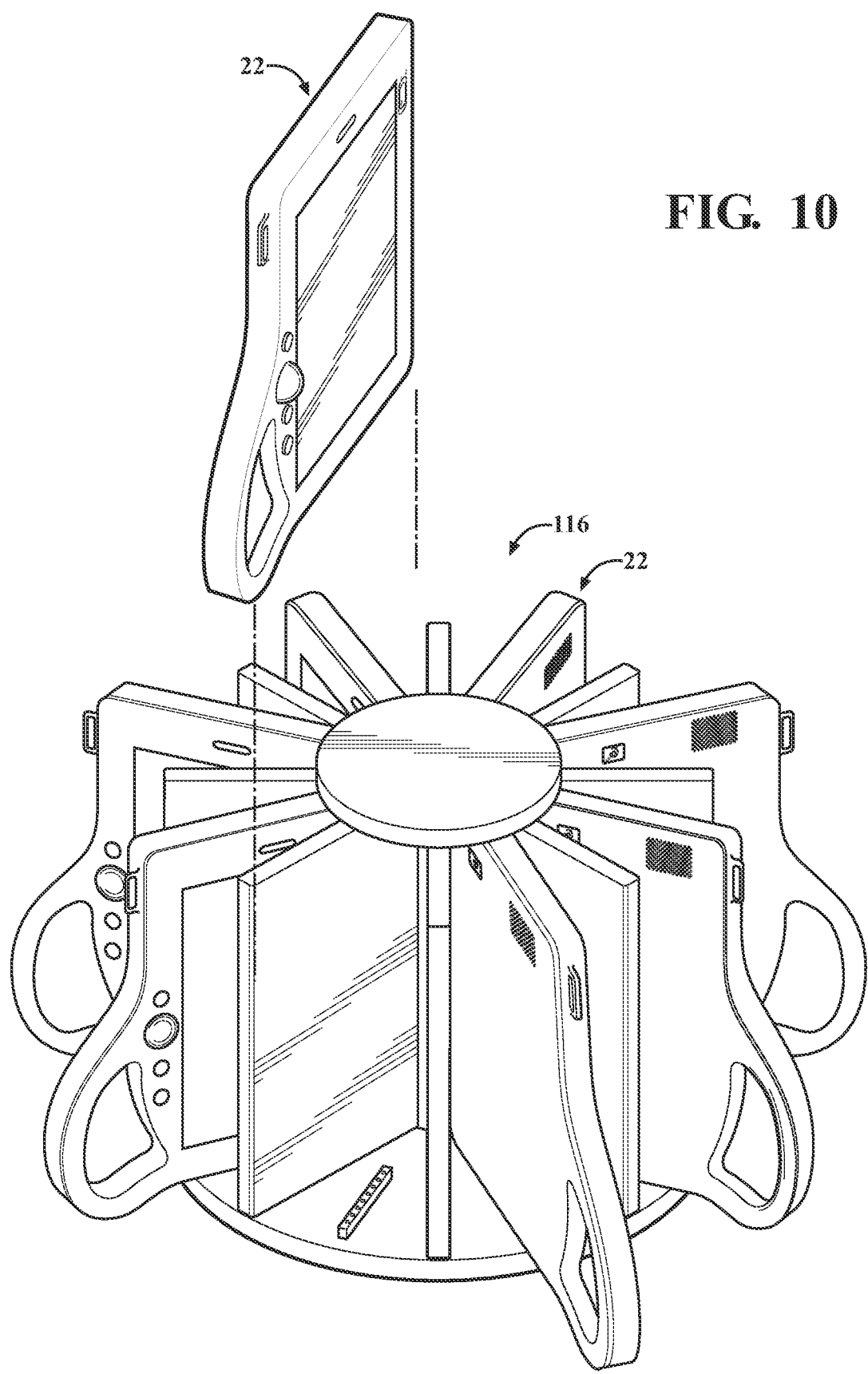
FIG. 10 is a perspective view of a carousel for a plurality of third components.

FIG. 10 is a perspective view of a carousel 116 for a plurality of third components 22. Each of the third components 22 can be stored in a slot of the carousel 116. The carousel 116 can include one or more locking mechanisms to retain the third components 22. Each lock can be selectively unlocked through the use of a biometric sensor. Each healthcare provider 14 can engage the particular biometric sensor to release his/her third component 22.

Figure 11:
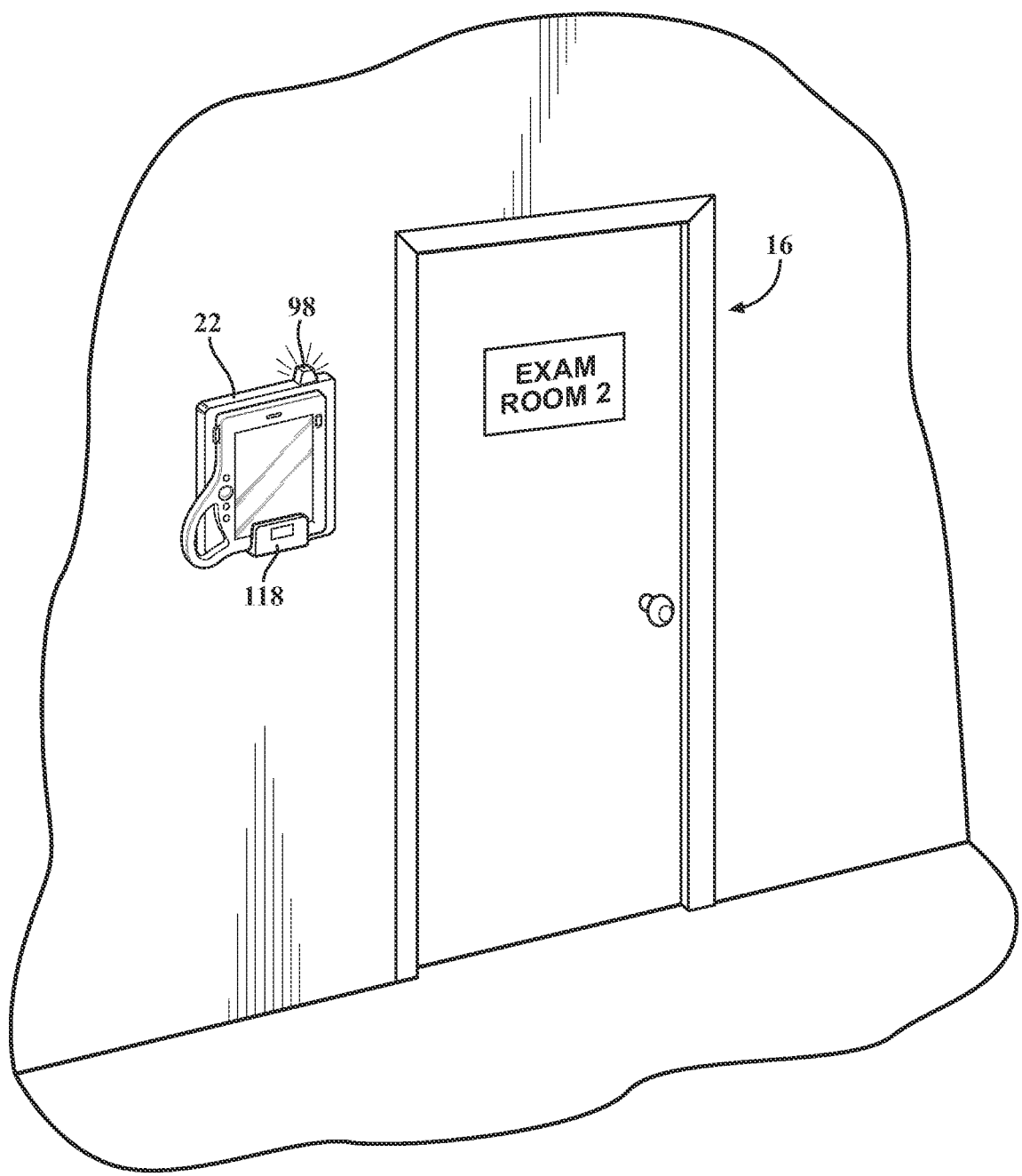
FIG. 11 is a perspective view of a third component positioned in a docking station outside of an examination room.

FIG. 11 is a perspective view of a third component 22 positioned in a docking station 118 outside of the examination room 16. The third component 22 can be placed in the docking station 118 and have downloaded the EHR of the patient 12 in the examination room 16. The LED 98 can be blinking to advise the healthcare provider 14 that the examination can begin.

Figure 12:
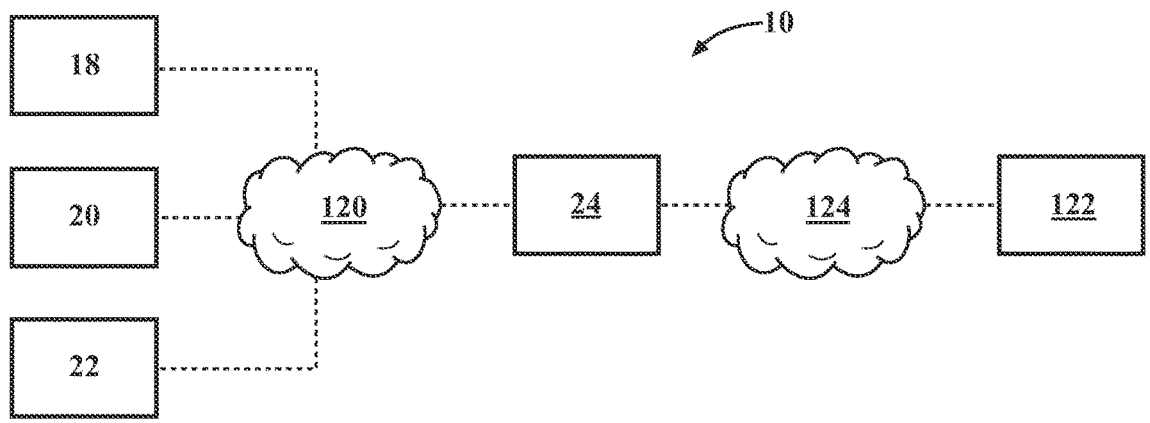
FIG. 12 is a diagram of a computing system including an exemplary computing device according to some implementations of the present disclosure.

Clinical data can be directly input via diagnostic instruments into the EHR wirelessly via the information technology system during the patient visit. FIG. 12 is a diagram of a computing system including an exemplary computing device 10 according to some implementations of the present disclosure. The components 18, 22, 24 can wirelessly communicate with the component 24 over a local network 120. The component 24 can wirelessly communicate with a fifth component 122 (another server) over a network 124. As used herein, the term "network" can include, but is not limited to, a Local Area Network (LAN), a Metropolitan Area Network (MAN), a Wide Area Network (WAN), the Internet, or combinations thereof. Embodiments of the present disclosure can be practiced with a wireless network, a hard-wired network, or any combination thereof.

Figure 13:
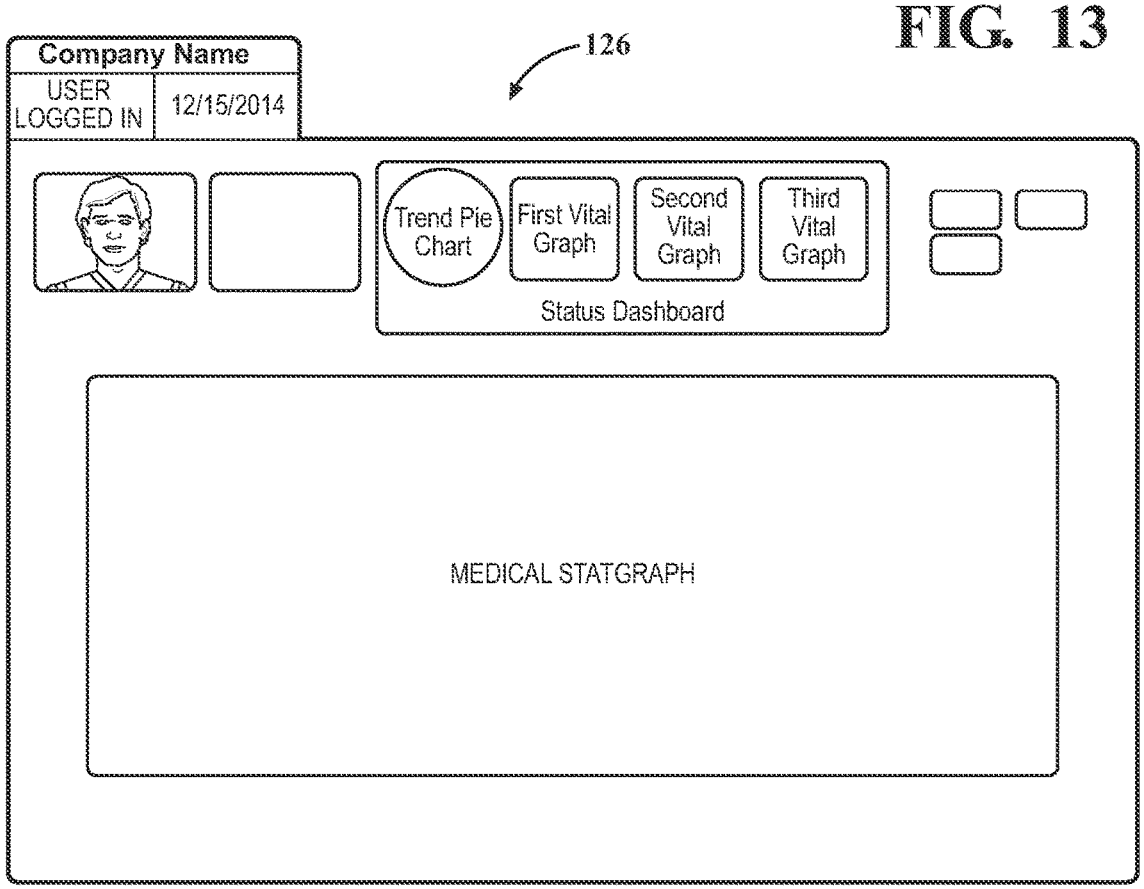
FIG. 13 is a screen shot of an exemplary graphic user interface according to some implementations of the present disclosure.

FIG. 13 is a screen shot of an exemplary graphic user interface (GUI) according to some implementations of the present disclosure, which can be displayed on the display 100. The content of the GUI 126 can include a portion for the display of the face of the patient 12, acquired from the EHR. This can allow the healthcare provider to confirm the identity of the patient 12. The GUI 126 can also display/confirm the identity of the healthcare provider 14. The GUI 126 can provide a plurality of input options for the entry of data defining the medical state of the patient 12. The GUI 126 can provide pull-down menus to ensure data is captured in a controlled format.

In one or more embodiments of the present disclosure, proximity of the patient's headset (the first component 18) to an interface of a diagnostic instrument (such as second component 20 or third component 22) can be utilized to collect and transmit information. This can be further used to verify that the information is being a linked to the correct patient by confirming that the unique identifying number associated with the headset close to the instrument matches the number on the tag linked to the EHR entry in the computer being used to compile that patient's visit record. As there is no longer a paper chart that travels with the patient through the office visit, the presence of the physical first component 18 helps to ensure that no misidentification occurs and yet maintains privacy and confidentiality.

As shown in FIG. 1, the patient 12 can be greeted by a doctor 14 and conducted to an examination or "pre-test" room 16 for a medical interview. The purpose of visit can be confirmed. The purpose of the visit can direct the medical interview. Depending on the required complexity suggested by visit purpose, the patient 12 can be asked a series of questions which are answered by selecting from prescribed response options. In this fashion, the components of a current medical statgraph, which includes a contemporary patient narrative (hereafter "CPN") is constructed. The technician can serve as a translator to assist the patient 12 in communicating their narrative within the framework of the EHR system.

In one or more embodiments of the present disclosure, patients who do not require face-to-face assistance may complete the CPN via a computer based interview in a secure area of the practice, and may electronically authorize importation of information from insurers, pharmacies and other providers. A keyboard/monitor interface can be used to record the communication and understanding of preliminary information such as notice of privacy practices, informed consent materials, as well as other policies. A signature pad or other biometric reader can be used to record authorizations and consents. Additionally, some pre-screening and visual tests (such as color perception) can be presented and performed via the monitor and a keyboard/mouse/joystick interface.

A detail example is provided below. A specific question structure and data options for an ophthalmology practice are described in tables set forth below and can guide history taking and examination, however the present disclosure is not limited to ophthalmology practices. In addition to CPN data, other categories of data can be collected. The data can include observed functional loss (hereafter "OFL"). The data can include direct examination findings (hereafter "DEF"). OFL positives or items can be constructed by exams conducted by a Technician and entered into prescribed data fields. DEF positives can be constructed using initial steps by a technician depending on level of skill, as well as subsequent steps by the doctor. Positives in CPN, OFL and DEF are listed and identified by nature, sub-nature and detail descriptors according to positives or deviations from what is expected or normal. The detail descriptors for each category can be of the following types: sub-nature, location, chronological correlations (onset, pattern, cycle), therapeutic correlations, environmental correlations, and functional adaptation correlations.

CPN is a subjective, patient reported description of psychic burden, pain and suffering. The categories of CPN can be aspects of subjective functional loss, aspects of sensorimotor anomaly, aspects of pain and discomfort, aspects of patient 12 observed abnormalities in appearance and anatomy, and aspects of history of trauma or past environmental exposure presenting an increased probability of injury, disease or reduced function. CPN positive items can be gathered as packets consisting of a core element describing the essential nature and sub-nature of the item, associated with a measure of severity or amplitude/magnitude and a group of detail descriptors providing descriptions relating to factors reported to have some correlation with the magnitude of the CPN item. Data associate with an exemplary CPN of an exemplary patient 12 is set forth in the table below:

TABLE 1

| CPN LOCATION | | | DETAIL DESCRIPTOR | | | | | | | |
|---|---|---|---|---|---|---|---|---|---|---|
| DESCRIPTION | | SEVERITY | | CHRONOLOGICAL | | | | CONTEXTUAL DESCRIPTION | | |
| NATURE | | | GRADIENT | DESCRIPTION | | | | | REMEDY | COM- |
| DESCRIPTION | SUB-NATURE | MAGNITUDE | DESCRIPTION GRADIENTS | ONSET | TREND | PATTERN | CYCLE | ASSOCIATIONS | & RESPONSE | PLICATIONS |
| One of: RFL ALGIA SMA OBAB1 OBAB2 | | | PRIMARY SIDE SECONDARY SIDE VERTICAL HORIZONTAL RADIAL | time/ date THIS ONSET FIRST EPISODE ONSET PEAK ONSET | | | cycle 1 cycle 2 | CORRELATION WITH: INGESTION ENVIRONMENT GENERAL ACTIVITY, ORGAN SPECIFIC ACTIVITY | CORRELATION WITH: RX OTC HOME PHYSICAL THERAPY, FUNCTIONAL ADAPTION TO SENSORY CHALLENGE | CORRELATION WITH: |

In response to the nature of the information captured within the CPN, computing device 10 can provide prompts to the healthcare provider 14 that tailor the steps of the rest of the medical encounter: technician exam, refractive services, same visit diagnostic tests, and doctor exam components.

The term "description" can be text entered by a doctor/technician or selected from a pull-down menu. The nature can be defined by a reported functional loss (hereafter "RFL"), algia (physical pain, discomfort or irritation), an SMA, and/or a patient observed abnormality (hereafter "OBAB"). A sensorimotor anomaly is an abstract disorder of sensation or voluntary movement.

OFL positive items are gathered as packets consisting of a core element describing the essential nature and sub-nature of the item, connected to a measure of severity or amplitude/magnitude. The categories of OFL are related to the system under study. In ophthalmology it could be divided in visual acuity, visual field, and other measures of richness of vision such as color perception, contrast sensitivity, and depth perception. Data associated with an exemplary OFL of an exemplary patient is set forth in the table below:

TABLE 2

| OFL | LOCATION DESCRIPTION NATURE DESCRIPTION | SUB-NATURE | SEVERITY MAGNITUDE |
|---|---|---|---|

DEF positive items are gathered as packets consisting of a core element describing the essential nature and sub-nature of the item, as well as a description of observed pathophysiology connected to a measure of severity or amplitude/magnitude. The categories of DEF are associated with anatomic location, classified based on observed pathophysiology findings and can, for example be labeled with attributes of increased or decreased presence, size, pigment, movement, circulatory supply, and/or inflammation. Data associate with an exemplary DEF of an exemplary patient 12 is set forth in the table below:

TABLE 3

| DEF | LOCATION DESCRIPTION NATURE DESCRIPTION | SUB-NATURE | PATHOPHYSIOLOGY | SEVERITY MAGNITUDE |
|---|---|---|---|---|

As set forth above, the present disclosure provides a method of managing an electronic health record and displaying the medical state of the patient 12 to the health care provider 14. The computing device 10, having one or more processors, can receive a first input. The first input can correspond to a first medical state of the patient 12 and include a first plurality of positives. Each of the plurality of positives can correspond to a deviation from a healthy state for a particular anatomical portion of the body of the patient and can be a numerical value.

The following table shows a set of data that can define an exemplary first input:

TABLE 4

| | A | B | C | D | E |
|---|---|---|---|---|---|
| 1 | | | Information elicited and input into EHR | | |
| 2 | | | | | |
| 3 | 1 | | Subjective: | | |
| 4 | | 1a | Reported function impairment of biological system affected by the disease (Deficit in function) | | |
| 5 | | | Acute symptom 1 | | |
| 6 | | | Floaters, left eye | | |
| 7 | | CPN | SPECIFIC (OCULAR) | | |
| 8 | | | | | |
| 9 | | | NATURE DESCRIPTION | TYPE | COMPLICATIONS |
| 10 | | | RFL | SCOTOMA -ISLAND | NA |
| 11 | | | | | |
| 12 | | | Acute symptom 2 | | |
| 13 | | | Photopsia, left eye | | |
| 14 | | CPN | SPECIFIC (OCULAR) | | |
| 15 | | | | | |
| 16 | | | NATURE DESCRIPTION | TYPE | COMPLICATIONS |
| 17 | | | RFL | DYSPHOTOPSIA-SPECTR | NA |
| 18 | | | | | |
| 19 | | | Chronic symptom 1 | | |
| 20 | | | Blurred vision for distance, both eyes, R more than L | | |
| 21 | | | | | |
| 22 | | CPN | SPECIFIC (OCULAR) | | |
| 23 | | | | | |
| 24 | | | NATURE DESCRIPTION | TYPE | COMPLICATIONS |
| 25 | | | RFL | BLUR FIXATION-FAR | NA |
| 26 | | | | | |
| 27 | | | Chronic symptom 2 | | |
| 28 | | | Blurred vision for near, both eyes, R more than L | | |
| 29 | | CPN | SPECIFIC (OCULAR) | | |
| 30 | | | | | |
| 31 | | | NATURE DESCRIPTION | TYPE | COMPLICATIONS |
| 32 | | | RFL | BLUR FIXATION-FAR | NA |

TABLE 4-continued

|   | F | G | H | I |
|---|---|---|---|---|
| 1 | Information elicited and input into EHR | | | |
| 2 | | | | |
| 3 | | | | |
| 4 | Reported function impairment of biological system affected by the disease (Deficit in function) | | | |
| 5 | | | | |
| 6 | | | | |
| 7 | MSN (SYMPTOMATIC) | | | Severity grade |
| 8 | | LOCATION DESCRIPTION | | |
| 9 | DYNAMIC | | SDB | |
| 10 | NEW OCCURRENCE | VISUAL FIELD | 6 | |
| 11 | | | | |
| 12 | | | | |
| 13 | | | | |
| 14 | MSN (SYMPTOMATIC) | | | |
| 15 | | LOCATION DESCRIPTION | | |
| 16 | DYNAMIC | | SDB | |
| 17 | NEW OCCURRENCE | VISUAL FIELD | 5 | |
| 18 | | | | |
| 19 | | | | |
| 20 | | | | |
| 21 | | | | |
| 22 | MSN (SYMPTOMATIC) | | | |
| 23 | | LOCATION DESCRIPTION | | |
| 24 | DYNAMIC | | SDB | |
| 25 | NEW OCCURANCE | VISUAL FIELD | 4 | |
| 26 | | | | |
| 27 | | | | |
| 28 | | | | |
| 29 | MSN (SYMPTOMATIC) | | | |
| 30 | | LOCATION DESCRIPTION | | |
| 31 | DYNAMIC | | SDB | |
| 32 | NEW OCCURANCE | VISUAL FIELD | 4 | |

Names of positives are set forth in cells B6, B13, B20, and B20; these names could have been selected from pull-down menus. The data set forth in cells below "Nature Description," "Type," "Complications," "Dynamic," "Location Description," and "Severity Grade" for each positive could have been selected from pull-down menus. Alternatively, in one or more embodiments of the present disclosure, the data in one or more of the cells could have been selected or suggested by the computing device 10 based on the data selected for other cells. For example, the "Severity Grade" can be determined by the computing device 10 based on the selection made for another of the categories. The computing device 10 can update the EHR of the patient 12 by adding the first input. The EHR can be stored in the memory associated with the fourth component (server) 24 or the server 122.

The computing device 10 can be compare the first plurality of positives with a plurality of different medical conditions each defined by a respective second plurality of positives. For example, the fourth component 24 or the server 122 can include memory storing a database of different medical conditions. Each medical condition can be defined by a plurality of positives. The positives found in the patient 12 can be compared with positives for each medical condition stored in the database.

The computing device 10 can group at least some of the first plurality of positives that collectively correlate to at least one of the plurality of different medical conditions and the respective second plurality of positives. For example, seven positives may be found for the patient 12. Four of those positives may also be positives of a first medical condition. The computing device 10 can group these four positives together, defining a problem bundle. One of the positives may be a positive of a second medical condition. The correlation between a positive and a medical condition can be historically recognized as strong and the single positive could also define a problem bundle. One or more positives may be positives of more than one medical condition and thus be part of more than one problem bundle. Each problem bundle can correspond to a particular medical condition.

The following table shows an exemplary set of problem bundles that can be identified in response to the exemplary first input:

TABLE 5

|   | J | K | L | M | N | O | P | Q | R | S | T | U | V |
|---|---|---|---|---|---|---|---|---|---|---|---|---|---|
|   | Problem Bundles | | | | | | | | | | | | |
| 1 | 1 | 2 | 3 | 4 | 5 | 6 | 7 | 8 | 9 | 10 | 11 | 12 | 13 |
| 2 | PVD OS | Moderate visual impairment related to cataracts | Early macular degeneration | Glaucoma suspect, low risk | Diabetic retinopathy, mild | Dry eyes, mild | Blepharitis mild | Blepharoptosis, moderate | Treatment with retinotoxic medication, | Uncorrected refractive error, mild | Diagnosis of Rheumatoid arthritis, typical | Diagnosis of Cardiovascular disease (hypertension), | Diagnosis of hypercholesterolemia, mild |

TABLE 5-continued

| | J | K | L | M | N | O | P | Q | R | S | T | U | V |
|---|---|---|---|---|---|---|---|---|---|---|---|---|---|
| | | | | | | | | | medium risk | | | typical | |
| 3 | Chief Complaint | | | | | | | | | | | | |
| 4 | | | | | | | | | | | | | |
| 5 | | | | | | | | | | | | | |
| 6 | | | | | | | | | | | | | |
| 7 | | | | | | | | | | | | | |
| 8 | | | | | | | | | | | | | |
| 10 | 6.00 | 0.00 | 0.00 | 0.00 | 0.00 | 0.0 | 0.00 | 0.00 | 0.00 | 0.00 | 0.00 | 0.00 | 0.00 |
| 11 | | | | | | | | | | | | | |
| 12 | | | | | | | | | | | | | |
| 13 | | | | | | | | | | | | | |
| 14 | | | | | | | | | | | | | |
| 15 | | | | | | | | | | | | | |
| 17 | 5.00 | 0.00 | 0.00 | 0.00 | 0.00 | 0.0 | 0.00 | 0.00 | 0.00 | 0.00 | 0.00 | 0.00 | 0.00 |
| 18 | | | | | | | | | | | | | |
| 19 | | | | | | | | | | | | | |
| 20 | | | | | | | | | | | | | |
| 21 | | | | | | | | | | | | | |
| 22 | | | | | | | | | | | | | |
| 23 | | | | | | | | | | | | | |
| 24 | | | | | | | | | | | | | |
| 25 | 0.50 | 1.00 | 0.50 | 0.00 | 0.00 | 1.0 | 0.00 | 0.00 | 0.00 | 1.00 | 0.00 | 0.00 | 0.00 |
| 26 | | | | | | | | | | | | | |
| 27 | | | | | | | | | | | | | |
| 28 | | | | | | | | | | | | | |
| 29 | | | | | | | | | | | | | |
| 30 | | | | | | | | | | | | | |
| 31 | | | | | | | | | | | | | |
| 32 | 0.50 | 2.00 | 1.00 | 0.00 | 0.00 | 0.5 | 0.00 | 0.00 | 0.00 | 0.00 | 0.00 | 0.00 | 0.00 |

Table 5 is an extension of Table 4. Thus, the computing device 10 can have determined that thirteen different problem bundles can be relevant to the patient 12 based on the positives found by examination. It is also noted that the severity grade can be allocated to one problem bundle or more than one problem bundle. In row thirty-two, the severity grad of the positive was selected to be equal to four and was allocated, by the computing device 10, among problem bundles in columns J, K, L, and O.

The computing device 10 can also assess the consistency among the problem bundles. The following table shows the inclusion of a column for a "mismatch" associated with problem bundles:

TABLE 6

| S | T | U | V | W | X | |
|---|---|---|---|---|---|---|
| 10 | 11 | 12 | 13 | | | 1 |
| Uncorrected refractive error, mild | Diagnosis of Rheumatoid arthritis, typical | Diagnosis of Cardiovascular disease (hypertension), typical | Diagnosis of hypercholesterolemia, mild | | | 2 |
| | | | | | | 3 |
| | | | | | | 4 |
| | | | | | | 5 |
| | | | | Combined total | mismatch | 6 |
| | | | | | | 7 |
| | | | | | | 8 |
| | | | | | | 9 |
| 0.00 | 0.00 | 0.00 | 0.00 | 6.00 | 0.00 | 10 |
| | | | | | | 11 |
| | | | | | | 12 |
| | | | | | | 13 |
| | | | | | | 14 |
| | | | | | | 15 |
| | | | | | | 16 |
| 0.00 | 0.00 | 0.00 | 0.00 | 5.00 | 0.00 | 17 |
| | | | | | | 18 |
| | | | | | | 19 |
| | | | | | | 20 |
| | | | | | | 21 |
| | | | | | | 22 |
| | | | | | | 23 |
| | | | | | | 24 |

TABLE 6-continued

| S | T | U | V | W | X | |
|---|---|---|---|---|---|---|
| 0.00 | 0.00 | 0.00 | 0.00 | 4.00 | 0.00 | 25 |
| | | | | | | 26 |
| | | | | | | 28 |
| | | | | | | 29 |
| | | | | | | 30 |
| | | | | | | 31 |
| 0.00 | 0.00 | 0.00 | 0.00 | 4.00 | 0.00 | 32 |

Table 6 is an extension of Tables 4 and 5. Zeros are set forth in the exemplary mismatch column, representing no mismatch, but for some positives a number other than zero could be set forth in the mismatch column. For example, the thirteen exemplary problem bundles set forth in Tables 4-6 (row 2, columns J-V) can be determined by the computing device 10 to be the "most likely problem bundles" or MLPBS applicable to the patient 12. Although not shown in the Tables 4-6, other positives could be applicable to the patient, but not be associated with any of the MLPBS. The patient 12 may allege other positives or other positives could be identified during examination that are not associated with any of the MLPBS. For such positives, the mismatch column would contain that same value as the value selected for the severity grade.

A mismatch can be assessed by the computing device 10 in several different ways. In one or more embodiments of the present disclosure, the computing device 10 can emit a message to the healthcare provider 14 in response to the indication of a mismatch. The healthcare provider 14 can reassess a positive associated with a mismatch. In one or more embodiments of the present disclosure, the computing device 10 can re-determine the MLPBS in response to the indication of a mismatch. The MLPBS can be selected so that the value of one mismatch or all mismatches are minimized. In one or more embodiments of the present disclosure, the computing device 10 can store in memory the combination of positives for further assessment in response to the indication of a mismatch. As data associated with more patients is collected, a new or revised problem bundle can be determined if a particular mismatch is repeatedly identified. The computing device 10 can thus engage in machine learning in response to the indication of a mismatch.

The computing device 10 can also determine MLPBS in response to ratios of the severity grades of various positives. For example, the computing device 10 can determine MLPBS in response to the ratio of severity grades of OFL positives to the severity grades of DEF positives. Alternatively, the computing device 10 can determine MLPBS in response to the ratio of severity grades of RFL positives to the severity grades of DEF positives. OFL positives can be less subjective and can therefore be given greater weight in some circumstances.

Figure 14:
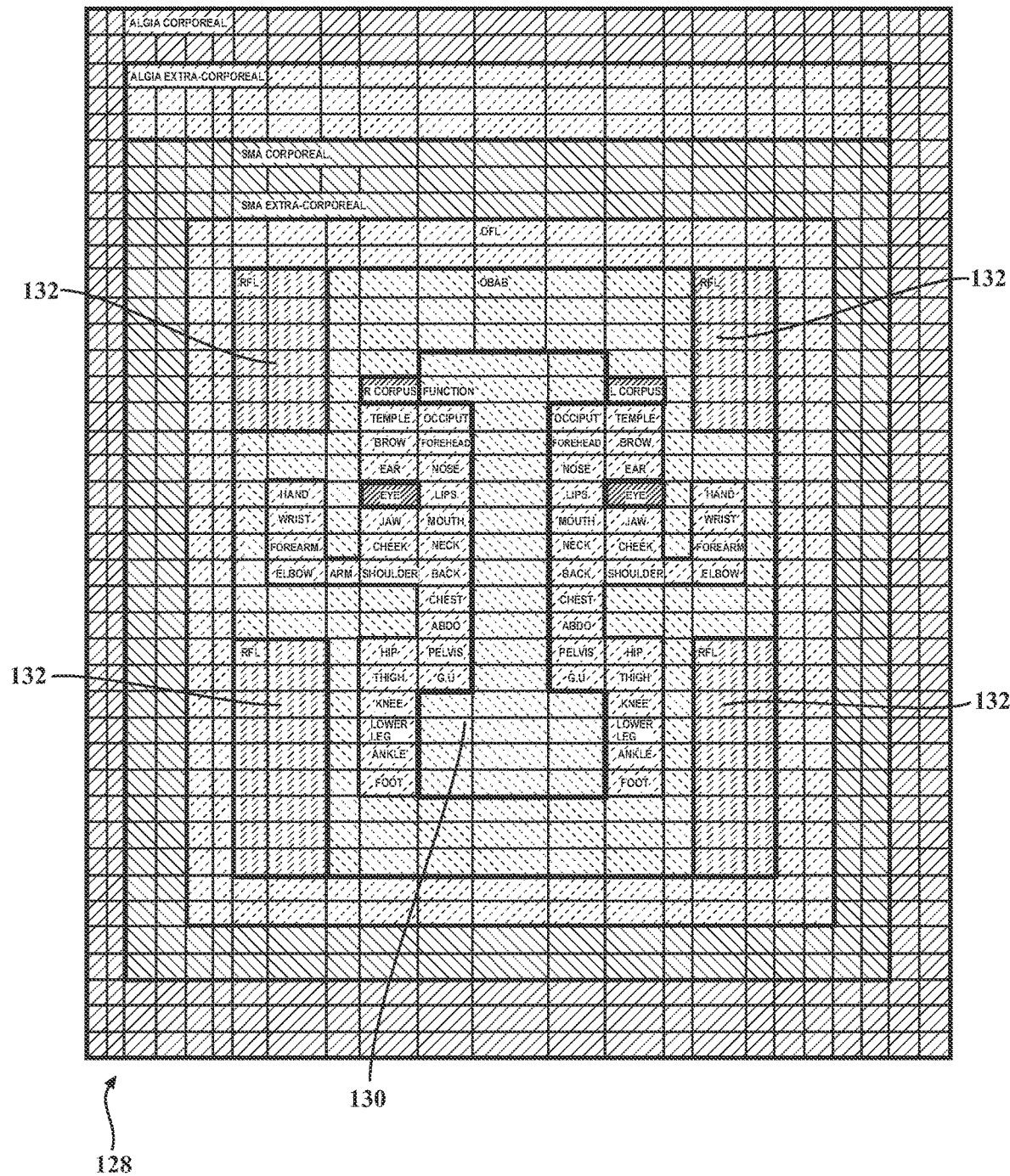
FIG. 14 is a top-down view of plane divided into a grid of a plurality of cells and wherein at least some of the plurality of cells correspond to the particular anatomical portions of the patient's body, wherein the plane is a two-dimensional medical statgraph for a system according to an exemplary embodiment of the present disclosure with a homunculus for direct examination findings (hereafter DEF), pockets for reported functional loss (hereafter RFL), and belts for sensorimotor anomaly (hereafter SMA), algia and trauma.

The positives elicited at the examination and interview with the patient 12 can be displayed by the display 100 or another display controlled by the computing device 10. The computing device 10 can control a display to display a plurality of objects. One of the displayed objects can be a medical statgraph. A medical statgraph is shown in FIG. 14 and referenced at 128. The medical statgraph 128 can be a planar, two dimensional representation of a human body or "homunculus" with surrounding "pockets" and circumferential "belts." The medical statgraph is also referred to herein as a homunculus plane. The homunculus plane 128 can be divided into a grid of a plurality of cells and wherein at least some of the plurality of cells correspond to the particular anatomical portions of the body of the patient 12. The various cross-hatching patterns correspond to different colors that the cells may be colored. A homunculus portion 130 (shown with a first shading pattern) itself can represent an area for placing and recording the anatomical location of DEF components. The pockets (shown with a first shading pattern) referenced at 132 can represent areas for describing RFL components. The successive layers of belts around the homunculus portion 130 represent areas for grouping and placement of other components of the medical statgraph 128 such as OBAB, OFL, algia, and trauma. Each cell on the two dimensional grid of the current medical statgraph 128 has an x, and y coordinate corresponding to the sub-nature and natures of a particular component of the medical statgraph 128.

In response to the existence of a positive, the computing device 10 will cause the display to display a node on the homunculus plane 128. Exemplary nodes are referenced in FIGS. 15 and 16 at 136, 138, 140, 150, and 152. At least one of the nodes will project away from the homunculus plane 128, from a cell that corresponds to the respective particular anatomical portion of the body of the patient 12. Each node will project away from the homunculus plane 128 a height proportional to the magnitude or severity of the positive. A positive having a severity grade of "6" will have a greater height than a having a severity grade of "5," "4," "3," etc.

Each node can define a respective cross-section in a plane parallel to the homunculus plane 128. The nodes 136 and 140 have a rectangular cross-section and node 138 has a circular cross-section. The shape of the cross-sections can be selected to convey information. For example, nodes having a rectangular cross-section can represent positives measured objectively and nodes having a circular cross-section can represent positives that are defined subjectively, such as node 136. Also, the nodes can be displayed in different colors to convey information. The respective nodes can also be displayed with different opacities, such as node 136.

Figure 15:
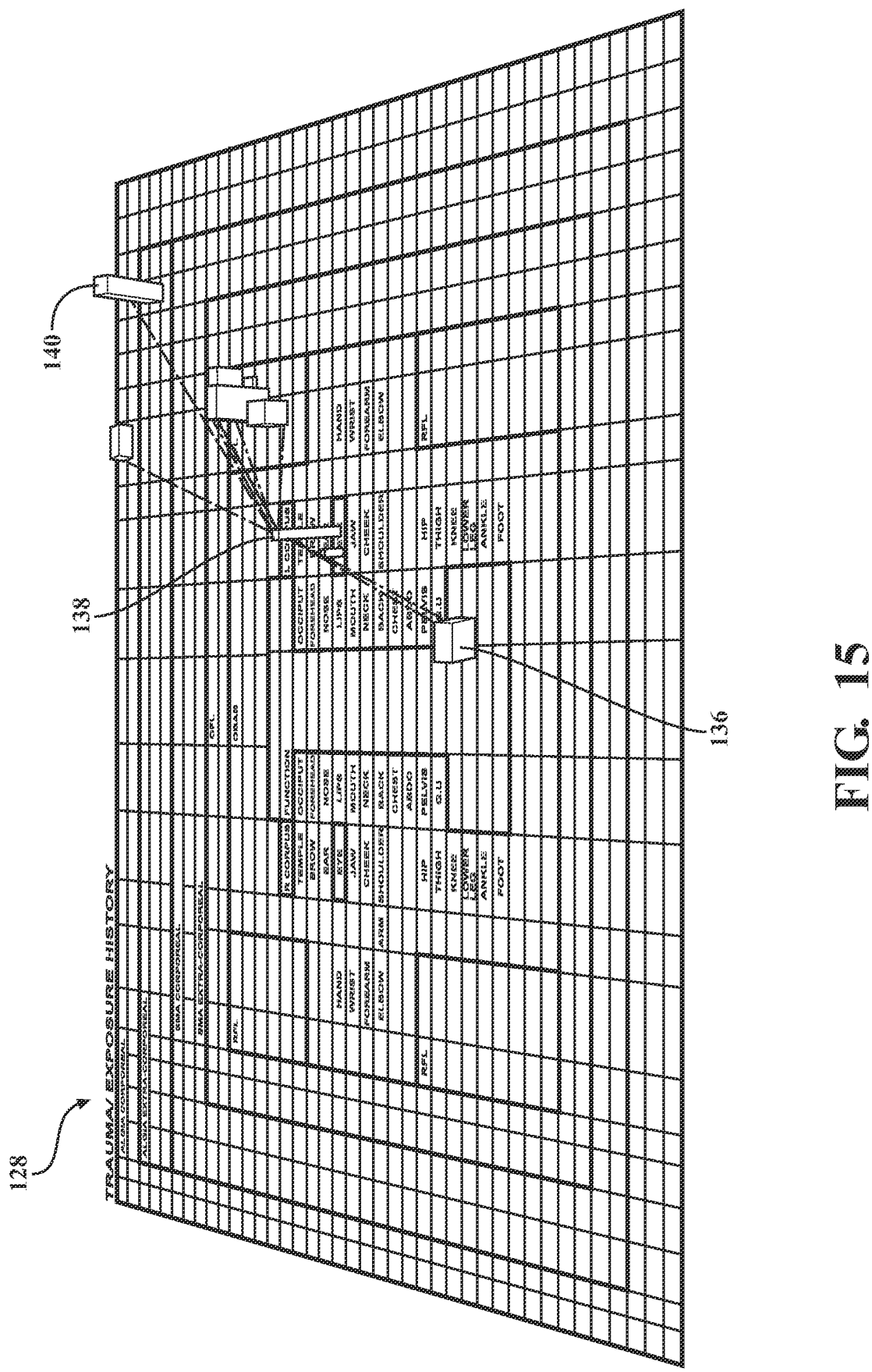
FIG. 15 is a perspective view of the plane shown in FIG. 14, with nodes projecting from the plane and axes extending between the nodes.
Figure 16:
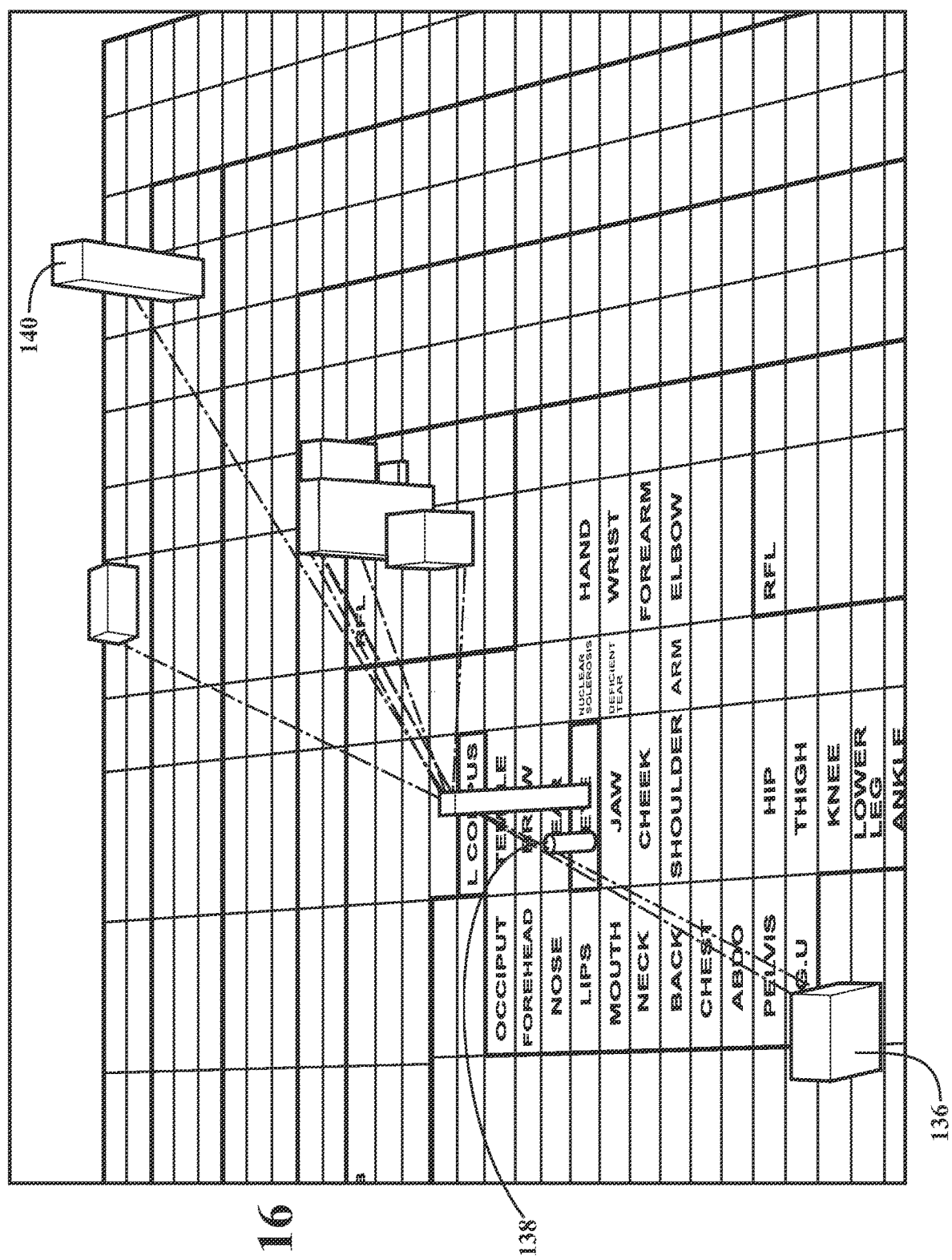
FIG. 16 is a magnified portion of FIG. 15.

FIG. 15 is a perspective view of the homunculus plane 128 shown in FIG. 14, with nodes projecting from the homunculus plane 128 and axes extending between the nodes. The computing device 10 can control a display to display an image such as shown in FIG. 15. FIG. 16 is a magnified portion of FIG. 15. The nodes are also shown in perspective view. Each of the axes interconnect at least two of the nodes.

The nodes within DEF, OFL, and CPN portions of the homunculus plane 128 will be displayed over the point or cell in the homunculus plane 128 used to describe their nature and sub-nature. Each such point or cell will have a link or "arrow" to an area or "bubble" which contains a detail descriptor of information in textual form.

Nodes in medical statgraph 10 can be linked by axes to enhance the clarity of problem bundles. Nodes or cells are overlay areas of the homunculus (human figure and its satellite regions) with the regions being juxtaposed to provide easy visualization of common and important patterns of diseases. The first two dimensions of nodes can be located on a two-dimensional map whose axes give information about (1) pathophysiological nature and sub-nature of the component element and (2) abstract or anatomical location of the component element. The height of the node in the third dimension represents the magnitude of the component element identified by the first two dimensions. Severity, extent, risk, acuteness and recalcitrance are examples of measures of "magnitude" for medical purposes and the elements of CPN, OFL and DEF can all be measured using standardized scales based on large populations. The node thus identified in three dimensions in relation to a homunculus, can be given additional attributes described by shape, size, color or luminosity to identify more information of the node such as correlations of chronology, therapy, environment, and/or functional adaptation.

The descriptors of the nodes in the first two axes can be classified and arranged to provide the maximum utility with minimum complexity for medical purposes for ease of visualize navigation. While each specialty will have its own combination of such components, examples suitable for ophthalmology have been given but can be generally adapted as they are derived from "first principals".

The logical connections between positive items linking problem bundles will form three dimensional shapes—whose conformity with established libraries serve to confirm the correctness of diagnoses and therapeutic plans. The construction of lines represents a method of demonstrating clinical decision making and inferences. The clinician can sort and arrange positives elicited in CPN, OFL and DEF into problem bundles in a process designed to be universally applicable and potentially all inclusive. The problem bundles can be arranged to coalesce duplicates, to filter "noise" and remove irrelevant items, and to succinctly communicate clinical thought and inferences to reviewers. The clinician can seek to link positive items into associated groups and create a logical bridge to therapy plans.

The layout of the homunculus may be fashioned so that easily cognizable information is conveyed by the placement, location and orientation of the shapes formed by the nodes and intersections comprising the most typical problem bundles. The distance of the nodes from a given plane may represent the severity so that incongruous elements are easily visible. The composition of the background homunculus may be engineered so that in the most common disease manifestations, the orientation of the intersecting lines between nodes is closest to linear. Similarly the effect of successful therapy can be visually confirmed by observing the movement of the problem bundle constituents towards the plane from which distance corresponds to severity.

Problem bundles can be arranged on and around a representation of the homunculus for ease of cognitive association and analysis. The homunculus is laid out to easily demonstrate disease process linked to observable changes at an anatomic location or abnormalities of biological functional systems associated with or conceptually juxtaposed with an anatomic location. A problem bundle can be created by grouping findings in one perspective type (CPN, OFL, or DEF) with findings in a second perspective type, and then with positives in a third perspective type. Problem bundles may consist of only one perspective type but only if no matching findings are discovered. A desirable approach can be to attempt to minimize the number of overall problem bundles by associating as many findings as possible.

The homunculus portion of the homunculus plane can be a two dimensional human figure for concrete anatomic descriptors and surrounding satellite regions representing functional and subjective elements of the medical status. The regions of the homunculus describe and group predefined values or potential values classified accordingly to their utility in analyzing and managing disease conditions and are arranged in regions or perspectives, further arranged into categories each of which has descriptors.

In one or more embodiments of the present disclosure, a database can include a pre-existing library of known disease conditions and their accompanying manifestations and symptoms and the EHR can attempt to link the positive elements of such conditions into problem bundles by joining the elements and connecting by lines. The color and thickness of the connecting line(s) can indicate the nature of a relationship such as "caused by", "secondary to", "associated with" etc.

The two dimensional orientation of the homunculus and its belts can be configured so that the most commonly associated elements for the most important disease processes fall in a straight linear path, with the line being parallel to the plane of the homunculus. The further the line is from the two-dimensional plane of the medical statgraph 10 along the z axis, the greater the overall severity of the problem bundle can be and hence its underlying disease conditions.

A clinician can be prompted to accept or reject suggested problem bundles. If proximate problem bundles do not exist in a standard problem bundle library, the clinician can be prompted to compile a custom problem bundle. Searches can be made through past medical statgraphs to check whether any current problem bundle has occurred before, in which case current problem bundle becomes "avatars" of these previously identified problem bundles. Otherwise, they are identified as new problem bundles.

For new problem bundles, the EHR can prompt the doctor with suggested therapy plans based on a library of therapy plans of ascending intensity matched to appropriate level of severity (or recalcitrance for pre-existing problem bundles). Several alternative options can exist within each intensity level based on patient idiosyncrasies such age, gender, ethnicity, allergy, formulary coverage etc. with the most cost effective and best matched therapy being presented first. After a therapy plan is activated by the clinician, tasks can be generated for staff by activation of therapy plan. Examples of action items in a therapy plan can be patient education information and instructions printed, prescriptions for medical drugs or devices generated and transmitted (printed, E-prescribed or E-fax), follow up appointments scheduled, additional tests and procedures scheduled and preliminary tasks for these services initiated (such as patient instructions, insurance pre-authorization, informed consent forms, operative report forms, test interpretation and report forms), correspondence and reports generated for other care-givers and insurance companies, medical restriction, FMLA and other paperwork generated for patient as necessary.

Problem bundles can be formed from the linkage of positive items in CPN, OFL and DEF. Positives are placed as points or nodes over a two dimensional figure to describe the nature, sub-nature and location of the items. The purpose of problem bundles is to define disease states (abnormal medical conditions and pathology) as collections of data items sorted into logical arrays and dimensions with components having nature and sub-nature described. The severity or magnitude of each item may be represented by intensity or location in the z axis.

Problem bundles can be visually defined by nodes or cells having respective heights connected by axes. Disease states derived from the medical consultation are formed into conglomerates termed problem bundles. Positive findings from areas of the history and of the examination are displayed and flagged as unanalyzed data for the supervising physician. These positive items can be elicited while determining the medical status and can be displayed as nodes or cells arranged in a three dimensional frame. Nodes are then connected to form problem bundles. The action of linking positive findings into problem bundles can be performed by the supervising physician who can be prompted to create links between positive items. Linkage patterns may be suggested by the system based on existing libraries of typically associated findings and the clinician may accept these suggestions or formulate their own linkage.

Problem bundles can be formed from the grouping of nodes. Excess nodes (those remaining unconnected) can be ignored with respect to active processing and archived for reference in case there are subsequent queries about the veracity of the diagnoses reached. For example, if therapy plans do not result in a projected medical status improvements.

FIG. 15 is sample three-dimensional representation of an exemplary medical statgraph of a patient with two ocular problems, each if which is connected with a systemic problem. FIG. 16 is a magnified portion of FIG. 15. In the example shown in FIG. 15, the patient has two ophthalmic problem bundles: (1) left cataract, associated with diabetes and (2) dry eye. More specifically, for the first condition, the patient has a nuclear sclerotic cataract of the left lens evidenced by the following positives:

CPN, RFL: blur at fixation for distance, blur fixation at near, dysphotopsia, desaturation, scotoma;

OFL: Snellen visual acuity reduced; and

DEF: slit lamp examination shows nuclear lenticular opacity.

For the second condition, the patient has dry eye on the left side evidenced by the following positives:

CPN, RFL: blur at fixation for distance, blur fixation at near, and dysphotopsia;

CPN, Algia: foreign body sensation (grittiness) of eye;

OFL: Snellen visual acuity reduced; and

DEF: slit lamp examination shows reduced tear film break up time.

Figure 17:
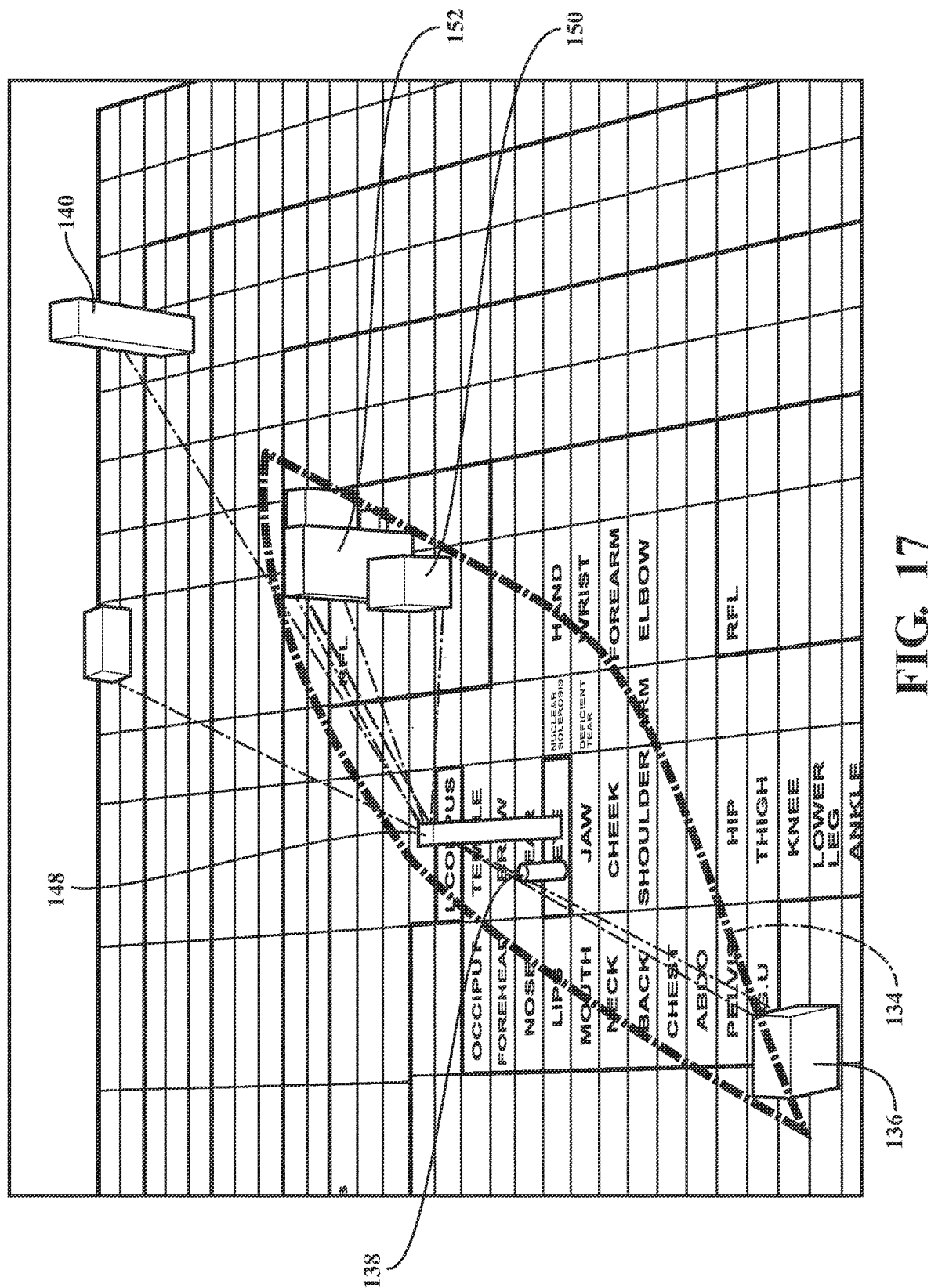
FIG. 17 is a view of the objects shown in FIG. 16 as well as a planar grouping object.

Referring now to FIG. 17, the computing device 10 can also control the display to display a planar bundling object 134 in perspective view. The planar bundling object 134 can envelope at least some of the first plurality of nodes. The exemplary planar bundling object 134 envelopes the nodes 136, 138, as well as other nodes. By enveloping, the planar bundling object 134 serves to wrap or cover, or to surround a group of nodes. The planar bundling object 134, in various embodiments, can be transverse and parallel to the homunculus plane 128 and at least partially spaced from the homunculus plane 128.

Figure 18:
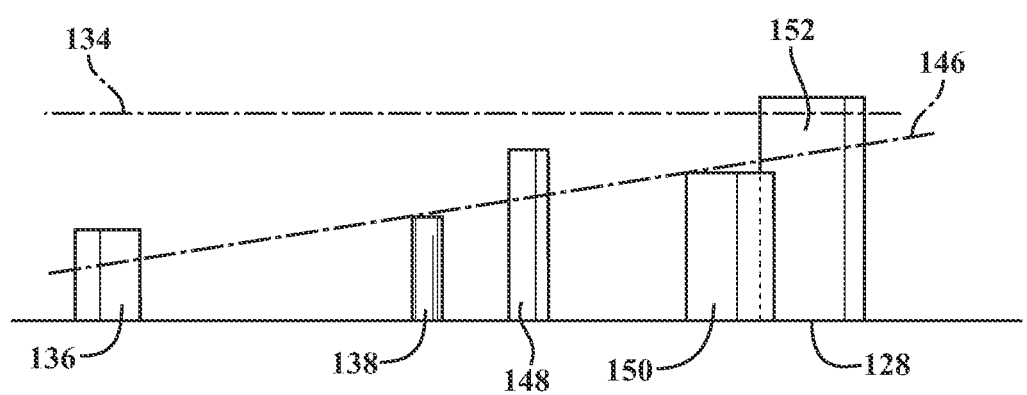
FIG. 18 is a side view of the objects shown in perspective view in FIG. 17.

The exemplary planar bundling object 134 is a linear segment circumscribing at least some of the first plurality of nodes. In one or more other embodiments of the present disclosure, the planar bundling object can be a plane of solid color intersecting at least some of the first plurality of nodes. FIG. 18 is a side view of the objects shown in perspective view in FIG. 17. FIG. 18 also includes a second planar bundling object 146. The computing device 10 can allow the healthcare provider 14 to orient the displayed objects as desired, including side views such as FIG. 18 where planar bundling objects can be viewed as a line and perspective views such as FIGS. 15-17. 14.

In FIG. 18, the second planar bundling object 146 can be plane that is arranged to at least partially intersect all of the nodes. The healthcare provider 14 can control the computing device 10 to change the display to orient the second planar bundling object 146 in perspective view. The angle between the second planar bundling object 146 and the homunculus plane 128 can convey information about the medical state of the patient 12 to the healthcare provider 14. For example, if all of the nodes are at substantially similar height, the second planar bundling object 146 and the homunculus plane 128 will be substantially parallel to one another. This can indicate a greater likelihood that the associated problem bundle is a condition suffered by the patient. On the other hand, if all of the nodes are at various heights, the second planar bundling object 146 (intersecting all of the nodes) will be skewed relative to the homunculus plane 128. This can indicate a lower likelihood that the associated problem bundle is the condition suffered by the patient.

These attributes of the display can also be extremely useful in tracking the efficacy of a course of treatment. For example, the computing device 10 can retrieve, from the electronic health record of the patient that is stored in memory, a second input. The second input can correspond to a prior medical state of the patient. The second input can include a plurality of positives, similar to the first input. Each of the positives corresponds to a deviation from a healthy state for a particular anatomical portion of the patient's body and is a numerical value, similar to the positives of the first input. It is noted that, as used herein, a particular anatomical portion of the patient's body corresponds to a physical anatomic location or its associated "belt" linking function on the homunculus plane 128 or subjective symptoms associated with that location.

The computing device 10 can display nodes corresponding to the positives of the second input concurrently with the nodes corresponding to the positives of the first input. Each of the nodes associated with the second input extend a height above the homunculus plane 128, similar to the nodes of the first input. The nodes associated with the second input can be overlaid on the nodes associated with the first input. The respective nodes can be differently colored and/or have different opacities. This will allow the healthcare provider 14 to readily see if the medical state of the patient 12 has improved or worsened. If the nodes associated with the first input are taller than the nodes associated with the second input, the medical state of the patient 12 has improved. If, however, the nodes associated with the first input are shorter than the nodes associated with the second input, the medical state of the patient 12 has worsened. Similarly, planar bundling objects generated at different times can be compared to quickly and readily assess changes in the condition of the patient 12.

While the present disclosure has been described with reference to an exemplary embodiment, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the appended claims. Further, the "present disclosure" as that term is used in this document is what is claimed in the claims of this document. The right to claim elements and/or sub-combinations that are disclosed herein as other present disclosures in other patent documents is hereby unconditionally reserved.

What is claimed is:

1. A method of displaying changes in a patient's medical state comprising:
receiving, at a computing device having one or more processors, a first input of a first set of data corresponding to a first medical state of the patient and including a first plurality of positives, wherein each of the first plurality of positives corresponds to a deviation from a healthy state for a particular anatomical portion of the patient's body and is a numerical value;
grouping, at the computing device, at least some of the first plurality of positives to a second plurality of positives wherein a plurality of different medical conditions are each defined by a respective second data set of one of more the second plurality of positives, wherein the at least some of the first plurality of positives collectively correlate to at least one of the plurality of different medical conditions and the respective second plurality of positives, thus defining a first plurality a problem bundles associated with the patient wherein each problem bundle is at least one of the first plurality of positives of the first set of data grouped to at least one of the second plurality of positives of the second set of data of a particular medical condition;
identifying, at the computing device, at least one mismatch with the first plurality of problem bundles associated with the patient during said grouping, wherein said at least one mismatch is at least one of the first plurality of positives of the patient that is not groupable to one of the second plurality of positives of at least one particular medical condition, said at least one of the first plurality of positives thus in the first set of data and not in the second set of data of the at least one particular medical condition;
displaying, on a display controlled by the computing device, a first statgraph that includes a plurality of objects including:
a homunculus plane in perspective view wherein the plane is divided into a grid of a plurality of cells and wherein at least some of the plurality of cells correspond to the particular anatomical portions of the patient's body,
a first plurality of nodes each in perspective view, each corresponding to one of the first plurality of positives, and each projecting away from the homunculus plane at the cell that corresponds to the respective particular anatomical portion of the patient's body, wherein a height of each of the first plurality of nodes from the homunculus plane corresponds to the respective numerical value,
a first plurality of axes each interconnecting at least two of the first plurality of nodes, and
a first planar bundling object in perspective view and enveloping at least some of the first plurality of nodes, the first planar bundling object being one of transverse and parallel to the homunculus plane and at least partially spaced from the homunculus plane;
receiving, at the computing device, a second input corresponding to a second medical state of the patient and including a third plurality of positives, wherein each of the third plurality of positives corresponds to a deviation from a healthy state for a particular anatomical portion of the patient's body and is a numerical value;
grouping, at the computing device, at least some of the third plurality of positives to a fourth plurality of positives wherein a plurality of different medical conditions are defined by one of more the fourth plurality of positives, wherein the at least some of the third plurality of positives collectively correlate to at least one of the plurality of different medical conditions and the respective fourth plurality of positives;
morphing, on the display controlled by the computing device, the displayed first statgraph into a second statgraph that includes:
the homunculus plane in perspective view,
a second plurality of nodes each in perspective view, each corresponding to one of the third plurality of positives, and each projecting away from the homunculus plane at the cell that corresponds to the respective particular anatomical portion of the patient's body, wherein a height of each of the second plurality of nodes from the homunculus plane corresponds to the respective numerical value, the first plurality of nodes morphed into the second plurality of nodes,
a second plurality of axes each interconnecting at least two of the second plurality of nodes, the first plurality of axes morphed into the second plurality of axes, and
a second planar bundling object in perspective view and enveloping at least some of the second plurality of nodes, the second planar bundling object being one of transverse and parallel to the homunculus plane and at least partially spaced from the homunculus plane, the first planar bundling object morphed into the second planar bundling object; and
reducing mismatches, at the computing device, via a machine learning algorithm, including:
repeatedly identifying, at the computing device, a first mismatch between a first positive and a first problem bundle involving a first medical condition, and
revising, at the computing device, in response to said repeatedly identifying, a second data set of the first medical condition to include the first positive and thereby eliminate the first mismatch from a subsequent grouping involving the first medical condition.

2. The method of claim 1 wherein each of the first plurality of nodes defines a respective cross-section in a plane parallel to the homunculus plane and wherein at least two of the first plurality of nodes have different cross-sections.

3. The method of claim 1 wherein each of the first plurality of nodes is displayed in a respective color and wherein at least two of the first plurality of nodes are displayed with different colors.

4. The method of claim 1 wherein each of the nodes is displayed with a respective opacity and wherein at least two of the first plurality of nodes are displayed with different opacities.

5. The method of claim 1 wherein said first planar bundling object is a linear segment circumscribing at least some of the first plurality of nodes.

6. The method of claim 1 wherein said first planar bundling object is a plane of solid color intersecting at least some of the first plurality of nodes.

7. The method of claim 1 further comprising:
retrieving, with the computing device, from the electronic health record of the patient, the electronic health record stored on a computer-readable medium, a second input corresponding to a prior medical state of the patient and including a fifth plurality of positives, wherein each of the fifth plurality of positives corresponds to a deviation from a healthy state for a particular anatomical portion of the patient's body and is a numerical value.

8. The method of claim 7 wherein said displaying is further defined as:
   displaying, on the display controlled by the computing device:
      a third plurality of nodes each in perspective view, each corresponding to one of the fifth plurality of positives, and each projecting away from the homunculus plane at the cell that corresponds to the respective particular anatomical portion of the patient's body, wherein a height of each of the third plurality of nodes from the homunculus plane corresponds to the respective numerical value.

9. The method of claim 8 wherein at least some of the third plurality of nodes and at least some of the first plurality of nodes are displayed overlaid with respect to one another.

10. The method of claim 8 wherein at least some of the third plurality of nodes and at least some of the first plurality of nodes are displayed in at least one of different colors and different opacities.

11. The method of claim 7 wherein said displaying is further defined as:
   displaying, on the display controlled by the computing device:
      a second planar bundling object in perspective view and enveloping at least some of the first plurality of nodes, the first planar bundling object being one of transverse and parallel to the homunculus plane and at least partially spaced from the homunculus plane.

12. The method of claim 11 wherein the second planar bundling object and the first planar bundling object are displayed in at least one of different colors and different opacities.

13. The method of claim 11 wherein the second planar bundling object and the first planar bundling object are displayed in at least one of parallel and transverse to one another.

14. The method of claim 11 further comprising:
   controlling the display, with the computing device, to change the viewing perspective to a side view such that at least one of the first planar bundling object and the second planar bundling object is displayed as a line.

15. The method of claim 1 wherein said displaying is further defined as:
   displaying, on the display controlled by the computing device:
      the homunculus plane in perspective view wherein the plane is divided into a grid of a plurality of cells and wherein a first group of the plurality of cells correspond to the particular anatomical portions of the patient's body and a second group of of the plurality of cells correspond to a belt of subjective symptoms surrounding the first group.

16. A system for displaying changes in a patient's medical state comprising:
   a display; and
   a computing device, comprising one or more processors and a non-transitory, computer readable medium storing instructions that, when executed by the one or more processors, cause the computing device to perform operations comprising:
      receiving a first input of a first set of data corresponding to a first medical state of the patient and including a first plurality of positives, wherein each of the plurality of positives corresponds to a deviation from a healthy state for a particular anatomical portion of the patient's body and is a numerical value;
      grouping at least some of the first plurality of positives to a second plurality of positives wherein a plurality of different medical conditions are each defined by a respective second data set of one of more the second plurality of positives, wherein the at least some of the first plurality of positives collectively correlate to at least one of the plurality of different medical conditions and the respective second plurality of positives, thus defining a first plurality a problem bundles associated with the patient wherein each problem bundle is at least one of the first plurality of positives of the first set of data grouped to at least one of the second plurality of positives of the second set of data of a particular medical condition;
      identifying, at the computing device, at least one mismatch with the first plurality of problem bundles associated with the patient during said grouping, wherein said at least one mismatch is at least one of the first plurality of positives of the patient that is not groupable to one of the second plurality of positives of at least one particular medical condition, said at least one of the first plurality of positives thus in the first set of data and not in the second set of data of the at least one particular medical condition;
      displaying, on the display, a plurality of objects including:
         a homunculus plane in perspective view wherein the plane is divided into a grid of a plurality of cells and wherein at least some of the plurality of cells correspond to the particular anatomical portions of the patient's body,
         a first plurality of nodes each in perspective view, each corresponding to one of the first plurality of positives, and each projecting away from the homunculus plane at the cell that corresponds to the respective particular anatomical portion of the patient's body, wherein a height of each of the first plurality of nodes from the homunculus plane corresponds to the respective numerical value,
         a first plurality of axes each interconnecting at least two of the first plurality of nodes, and
         a first planar bundling object in perspective view and enveloping at least some of the first plurality of nodes, the first planar bundling object being one of transverse and parallel to the homunculus plane and at least partially spaced from the homunculus plane;
      receiving, at the computing device, a second input corresponding to a second medical state of the patient and including a third plurality of positives, wherein each of the third plurality of positives corresponds to a deviation from a healthy state for a particular anatomical portion of the patient's body and is a numerical value;
      grouping, at the computing device, at least some of the third plurality of positives to a fourth plurality of positives wherein a plurality of different medical conditions are defined by one of more the fourth plurality of positives, wherein the at least some of the third plurality of positives collectively correlate to at least one of the plurality of different medical conditions and the respective fourth plurality of positives;
      morphing, on the display controlled by the computing device, the displayed first statgraph into a second statgraph that includes:
         the homunculus plane in perspective view,
         a second plurality of nodes each in perspective view, each corresponding to one of the third plurality of positives, and each projecting away from the homunculus plane at the cell that corresponds to the respective particular anatomical portion of the patient's body, wherein a height of each of the second plurality of nodes from the homunculus plane corresponds to the respective numerical value, the first plurality of nodes morphed into the second plurality of nodes, a second plurality of axes each interconnecting at least two of the second plurality of nodes, the first plurality of axes morphed into the second plurality of axes, and a second planar bundling object in perspective view and enveloping at least some of the second plurality of nodes, the second planar bundling object being one of transverse and parallel to the homunculus plane and at least partially spaced from the homunculus plane, the first planar bundling object morphed into the second planar bundling object; and reducing mismatches, at the computing device, via a machine learning algorithm, including:

repeatedly identifying, at the computing device, a first mismatch between a first positive and a first problem bundle involving a first medical condition, and revising, at the computing device, in response to said repeatedly identifying, a second data set of the first medical condition to include the first positive and thereby eliminate the first mismatch from a subsequent grouping involving the first medical condition.

17. The system of claim 16 wherein said computing device is further defined as comprising:

a first component being a device wearable by the patient, said first component including transceiver, a speaker, and a microphone.

18. The system of claim 17 wherein said computing device is further defined as comprising:

a second component being a stylus including one or more transducers and a transceiver.

19. The system of claim 18 wherein said computing device is further defined as comprising:

a third component being a tablet including a transceiver and wherein said display is mounted in said tablet.

20. A computer program product comprising program code stored on a non-transitory computer-readable medium, which when executed by a computing device having one or more processors, enables the computing device to implement a method of displaying changes in a patient's medical state to a health care provider by performing actions including:

receiving, at a computing device having one or more processors, a first input of a first set of data corresponding to a first medical state of the patient and including a first plurality of positives, wherein each of the plurality of positives corresponds to a deviation from a healthy state for a particular anatomical portion of the patient's body and is a numerical value;

grouping, at the computing device, at least some of the first plurality of positives to a second plurality of positives wherein a plurality of different medical conditions are each defined by a respective second data set of one or more the second plurality of positives, wherein the at least some of the first plurality of positives collectively correlate to at least one of the plurality of different medical conditions and the respective second plurality of positives, thus defining a first plurality a problem bundles associated with the patient wherein each problem bundle is at least one of the first plurality of positives of the first set of data grouped to at least one of the second plurality of positives of the second set of data of a particular medical condition; and identifying, at the computing device, at least one mismatch with the first plurality of problem bundles associated with the patient during said grouping, wherein said at least one mismatch is at least one of the first plurality of positives of the patient that is not groupable to one of the second plurality of positives of at least one particular medical condition, said at least one of the first plurality of positives thus in the first set of data and not in the second set of data of the at least one particular medical condition;

displaying, on a display controlled by the computing device, a plurality of objects including:

a homunculus plane in perspective view wherein the plane is divided into a grid of a plurality of cells and wherein at least some of the plurality of cells correspond to the particular anatomical portions of the patient's body, a first plurality of nodes each in perspective view, each corresponding to one of the first plurality of positives, and each projecting away from the homunculus plane at the cell that corresponds to the respective particular anatomical portion of the patient's body, wherein a height of each of the first plurality of nodes from the homunculus plane corresponds to the respective numerical value, a first plurality of axes each interconnecting at least two of the first plurality of nodes, and a first planar bundling object in perspective view and enveloping at least some of the first plurality of nodes, the first planar bundling object being one of transverse and parallel to the homunculus plane and at least partially spaced from the homunculus plane;

receiving, at the computing device, a second input corresponding to a second medical state of the patient and including a third plurality of positives, wherein each of the third plurality of positives corresponds to a deviation from a healthy state for a particular anatomical portion of the patient's body and is a numerical value;

grouping, at the computing device, at least some of the third plurality of positives to a fourth plurality of positives wherein a plurality of different medical conditions are defined by one or more the fourth plurality of positives, wherein the at least some of the third plurality of positives collectively correlate to at least one of the plurality of different medical conditions and the respective fourth plurality of positives;

morphing, on the display controlled by the computing device, the displayed first statgraph into a second statgraph that includes:

the homunculus plane in perspective view, a second plurality of nodes each in perspective view, each corresponding to one of the third plurality of positives, and each projecting away from the homunculus plane at the cell that corresponds to the respective particular anatomical portion of the patient's body, wherein a height of each of the second plurality of nodes from the homunculus plane corresponds to the respective numerical value, the first plurality of nodes morphed into the second plurality of nodes, a second plurality of axes each interconnecting at least two of the second plurality of nodes, the first plurality of axes morphed into the second plurality of axes, and a second planar bundling object in perspective view and enveloping at least some of the second plurality of nodes, the second planar bundling object being one of transverse and parallel to the homunculus plane and at least partially spaced from the homunculus plane, the first planar bundling object morphed into the second planar bundling object; and reducing mismatches, at the computing device, via a machine learning algorithm, including:

repeatedly identifying, at the computing device, a first mismatch between a first positive and a first problem bundle involving a first medical condition, and revising, at the computing device, in response to said repeatedly identifying, a second data set of the first medical condition to include the first positive and thereby eliminate the first mismatch from a subsequent grouping involving the first medical condition.

* * * * *